United States Patent [19]

Virta et al.

[11] Patent Number: 5,776,681
[45] Date of Patent: Jul. 7, 1998

[54] METHOD FOR DETERMINING A METAL PRESENT IN A SAMPLE

[76] Inventors: Marko Virta, Hämeenkatu 12 B 27, Turku, Finland, 20500; Matti Karp, Tapulikatu 6 A 22, Turku, Finland, 20810

[21] Appl. No.: 525,532

[22] PCT Filed: Jan. 17, 1995

[86] PCT No.: PCT/FI95/00017

§ 371 Date: Sep. 15, 1995

§ 102(e) Date: Sep. 15, 1995

[87] PCT Pub. No.: WO95/19446

PCT Pub. Date: Jul. 20, 1995

[30] Foreign Application Priority Data

Jan. 17, 1994 [FI] Finland ................... 940225

[51] Int. Cl.$^6$ .............. C12Q 1/68; C07H 21/04; C12N 15/63
[52] U.S. Cl. .............. 435/6; 435/320.1; 435/252.3; 435/69.1; 536/23.1
[58] Field of Search .............. 435/6, 320.1, 252.3, 435/69.1; 536/23.1

[56] References Cited

FOREIGN PATENT DOCUMENTS

| | | |
|---|---|---|
| 0 496 027 A1 | 7/1991 | European Pat. Off. |
| 0 524 448 A1 | 6/1992 | European Pat. Off. |
| 0 516 443 A1 | 12/1992 | European Pat. Off. |
| WO90/08836 | 8/1990 | WIPO |
| WO90/12887 | 11/1990 | WIPO |
| WO92/15687 | 9/1992 | WIPO |
| WO93/03179 | 2/1993 | WIPO |
| WO93/11257 | 6/1993 | WIPO |

OTHER PUBLICATIONS

07/768741 Karp and Korpela.

Belas et al., "Bacterial Bioluminescence: Isolation and Exprssion of the Luciferase Genes from Vibrio harveyi" *Science*, vol. 218, 791–793.

Boylann et al., "Fused Bacterial Luciferase Subunits Catalyze Light Emission in Eukaryotes and Prokaryotes" *J. Biol Chem.*, vol. 264, 1915–1918 (1989).

Chalfie et al., "Green Florescent Protein as a Marker for Gene Expression" *Science*, vol. 263, 802–805 (1994).

(List continued on next page.)

*Primary Examiner*—W. Gary Jones
*Assistant Examiner*—Amy Atzel
*Attorney, Agent, or Firm*—Lahive & Cockfield, LLP

[57] ABSTRACT

The invention relates to a method for determining a metal present in a sample, in which method a) a recombinant DNA plasmid the copy number of which is under the control of a promoter regulatable by the metal is transferred into the cell, or a recombinant DNA plasmid the copy number of which can be varied between 1 and 2000/cell is transferred into the cell, and the plasmid contains as a marker protein a DNA sequence coding for a virus, procaryotic cell or eucaryotic cell protein or for a portion thereof essential for its biological activity, the expression of the DNA sequence being under the control of a promoter regulatable by the metal and being controlled by negative and/or positive feedback;

b) the cell containing the recombinant DNA plasmid is contacted with a metal-containing sample;

c) the metal is allowed to affect for a suitable time the cell which contains the recombinant DNA plasmid, whereafter the amount of recombinant DNA plasmid or the amount of protein encoded by it is determined by either physical or chemical means;

d) the amount of recombinant DNA plasmid or the protein encoded by it is compared by chemical or physical means to a control test in which metal was not present and/or it was present in a known amount in a reaction, whereby the presence and/or amount of the metal can be determined.

34 Claims, 15 Drawing Sheets

OTHER PUBLICATIONS

Condee and Summers, "A mer–lux Transcriptional Fusion for Real–time Examination of In Vivo Gene Expression Kinetics and Promoter Response to Altered Superhelicity," *J. Bacteriol.*, vol. 174, No. 24, 8094–8101 (1992).

Corbisier et al., "luxAB gene fusions with the arsenic and cadmium resistance operons of *Staphylococcus aureus* plasmid pI 258," *FEMS Microbiol. Lett.*, vol. 110, 231–238 (1993).

DeWet et al., "Firefly Luciferase Gene: Structure and Expression in Mammalian Cells" *Mol. Cell. Mol. Cell. Biol.*, vol. 7, 725–737 (1987).

Frackman et al., "Cloning, Organization, and Expression of the Bioluminescence Genes of Xenorhabdus luminescens" *J. Bacteriol.*, vol. 172, 5767–5773 (1990).

Francisco et al., "Specific Adhesion and Hydrolysis of Cellulose by Intact Escherichia coli Expressing Surface Anchored Cellulase or Cellulose Binding Domains" *Bio/Technology*, vol. 11, 491–495 (1993).

Gilkes et al., "Precise Excision of the Cellulose Binding Domains from Two Cellulomonas fimi Cellulases by a Homologous Protease and the Effect on Catalysis" *J. Biol. Chem.*, vol. 263, 10401–10407 (1988).

Griffin et al., "Cloninng and DNA sequence of the mercuric–and organomercurial–resistance determinants of plasmid pDU1358" *Proc. Natl. Acad. Sci. USA*, vol. 84, 3112–3116 (1987).

Haefeli et al., "Plasmid–Determined Silver Resistance in Pseudomonas stutzeri Isolated from a Silver Mine" *J. Bacteriol.*, vol. 158, 389–392 (1984).

Hamer and Walling, "Regulation In Vivo of a Cloned Mammalian Gene: Cadmium Induces the Transcription of a Mouse Metallothionein Gene in SV40 Vectors" *J. Mol. Appl. Genet.*, vol. 1, 273–288 (1982).

International Search Report, International Application PCT/FI 95/00017; Filing date 17 Jan. 1995.

Karp, "Expression of bacterial luciferase genes from vibrio harvey in Bacillus subtilis and in Escherichia coli" *Biochem. Biophys. Acta*, vol. 1007, 84–90 (1989).

Karp et al. "A sensitive model system for in vivo monitoring of baculovirus gene expression in single infected insect cells," *Bio/Technology*, vol. 10, 565–569 (1992).

Lampinen et al., "Expression of luciferase genes from differnent origins in Bacillus subtilis" *Mol. Gen. Genet.*, vol. 232, 498–504 (1992).

Mergeay et al., "*Alcaligenes eutrophus* CH34 Is a Facultative Chemolithotroph with Plasmid–Bound Resistance to Heavy Metals" *J. Bacteriol.*, vol. 162, 328–334 (1985).

Misra et al., "Mercuric ion–resistance operons of plasmid R100 and transposon Tn501: The begining of the operon including the regulatory region and the first two structural genes" *Proc. Natl. Acad. Sci. USA*, vol. 81, 5975–5979 (1984).

NiBhriain et al., Tn5 Insertion Mutations in the Mercuric Ion Resistance Genes Derived from Plasmid R100? *J. Bacteriol.*, vol. 155, 690–703 (1983).

Nies, "CzcR and CzcD, Gene Products Affecting Regulation of Resistance to Cobalt, Zinc, and Cadmium (czc System) in Alcaligenes eutrophus" *J. Bacteriol.*, vol. 174, 8102–8110 (1992).

Nies et al., Nucleotide Sequence and Expression of a Plasmid–encoded Chromate Resistance Determinant from Alcaligenes eutrophus *J. Biol. Chem.*vol. 265, 5648–5653 (1990).

Novick and Roth, "Plasmid–linked Resistance to Inorganic Salts in Staphlococcus aures"*J. Bacteriol.*, vol. 95, 1335–1342 (1968).

Prasher et al., "Primary structure of the Aequorea victoria green–fluorescent protein" *Gene*, vol. 111, 229–233 (1992).

Thompson et al., "Cloning and expression of CDNA for the luciferase from the marine ostracod Vargula hilgendorfii" *Proc. Natl. Acad. Sci. USA*, vol. 86, 6567–6571 (1989).

Wu and Rosen, "The ArsR protein is a trans–acting regulatory protein" *Mol. Microbiol.*, vol. 5, 1331–1336 (1991).

METHOD FOR DETERMINING A METAL PRESENT IN A SAMPLE

The invention relates to a biotest in which the metal content is determined qualitatively and/or quantitatively from a liquid, gaseous, or solid sample by means of genetically manipulated cells.

Methods in which living cells or organisms are used as tools are in general called biotests. Many of the biotests developed utilize bacterial or yeast cells. A great deal of hope and interest have been placed on the use of microbes as rapid tests for heavy-metal residues. Since microbiological methods utilize bacteria or spores of bacteria, the sensitivity of the test bacterium to a heavy metal is of crucial importance in these methods. Up to the present it has been necessary to make compromises in the selection of suitable test microbes, since, for example, high sensitivity to heavy metals and other properties required of a test microbe have not necessarily been properties of one and the same bacterial strain.

The use of microbes in testing for heavy-metal residues is limited above all by the slow performance and insensitivity of the methods. Since the methods in one way or another always control the growth of the test microbes, it is inconceivable that a test could be performed in a time shorter than one hour. This is due to the fact that, even at its most rapid, microbial growth is slow. Furthermore, in a number of tests the microbes are freeze-dried microbes or spores; this slows down the performing of the tests even more. The present-day microbiological heavy-metal tests are not capable of determining single heavy metals or their groups; instead, they detect all toxic heavy metals to which the microbe concerned is sensitive.

Determination methods which are based on the measuring of bioluminescence, i.e. the production of light, have also been developed. In seas there are, living as planktonic populations or in a symbiosis with fish, a number of different bacterial strains which produce light as a byproduct of their metabolism. The production of light is accounted for by an enzyme called luciferase, the chemical reaction of its catalysis being as follows:

wherein the reduced flavin mononucleotide reacts with a long-chain aldehyde and oxygen, forming the corresponding oxidized products and light at a wavelength of 490 nm. The optimum temperature for bacterial luciferase is in general approx. 25° C., and it is very rapidly inactivated at the physiological temperature 37° C.

A method (trade name Microtox™), available even commercially and utilizing *Photobacterium fischeri* bacteria measures the overall toxicity of the environment (Bulich and Greene, 1979, International Symposium on Analytical Applications of Bioluminescence and Chemiluminescence. State Printing and Publishing, Westlake Village, Calif., pp. 193–211). The said bacterial cells used in the determination have been freeze-dried, and after rehydration they can be used for measuring, among other things, heavy-metal residues in general at a micromolar sensitivity level simply by measuring changes in the intensity of light, which changes correlate with the toxicity of the environment. The sample to be investigated and the bacteria are incubated together, and the presence of toxic substances is detected from the lowered luminescence level of the bacteria as compared with a control sample. The method has a number of drawbacks, the worst perhaps being a continuous and rapid luminescence decrease, which is in general compensated for in the test by using apparatus technology. This results in very expensive apparatus. The method also requires high salinity (3%), which has been shown to reduce the toxic effect of certain substances. The method is also nonspecific, and it reacts in the same manner to a number of heavy metals and other environmental toxins.

The gene mechanisms responsible for luminescence properties can also be transferred into other organisms by modern genetic engineering techniques, and thus a previously dark cell can be caused to emit light in the manner of the original bioluminescent bacterial cell (Belas et al., Science, 218, 791–793). These methods utilize luciferase genes isolated from luminescent *P. fischeri* and *Vibrio harveyi*, transferred into laboratory strains of *Escherichia coli*. Luciferase genes isolated from the only bioluminescent bacterium living on land, *Xenorhabdus luminescens* (Frackman et al., 1990, J. Bacteriol., 172, 5767–5773), the protein coded by them also being resistant to heat, can be mentioned as a special case. Such new luminescent cells can also be used for measuring the concentrations of environmental toxins (Karp and Korpela, FI patent 88309), and usually these methods are many times more efficient than the Microtox™ method. Also other organisms, procaryotic or eucaryotic cells, can be harnessed for the detection of toxins. For example, the gram-positive Bacillus subtilis bacterium can be transformed with luciferase genes (Karp, 1989, Biochem. Biophys. Acta, 1007, 84–90) and be used, for example, for measuring the presence and concentration of an antibiotic or heavy metal toxic to the bacterial cell (Karp and Korpela, FI patent 88309, U.S. patent application Ser. No. 768 741). A study published in 1989 (Boylan et al., 1989, J. Biol. Chem., 264, 1915–1918) can be mentioned as an example of the capacity of a eucaryotic cell to luminesce with the aid of bacterial luciferase genes.

Luciferase genes may also be placed under the control of genetic control elements responding to heavy metals, in which case the said control element will activate the synthesis of luciferase protein in the presence of a heavy metal. Under the effect of a heavy metal the said bacteria begin to produce light, the amount of which is directly proportional to the amount of heavy metal present. The theoretical basis for this method consists of the genetic systems developed by bacteria resistant to natural heavy metals, which systems change or effectively eliminate heavy metals so that the bacterium is capable of surviving at high concentrations of heavy metals. Often such elements are located in genetic elements outside the bacterial chromosome, i.e. in so-called plasmids, which are detectable in, among others, the *Staphylococcus aureus* (Novick and Roth, 1968, J. Bacteriol., 95, 1335–1342) or *Alcaligenes eutrophus* bacteria (Mergeay et al., 1985, J. Bacteriol., 162, 328–334). In these systems, often an unknown repressor changes its conformation in the presence of a heavy metal specific for it, whereupon a synthesis which changes or eliminates the metal can start. Such a control element can be transferred by genetic engineering techniques to control the expression of some foreign gene, for example in front of the *E. coli* bacterium lacZ gene, much used as a so-called reporter gene (Livrelli et al., 1993, J. Biol. Chem., 268, 2623–2631). Other much used reporter genes include cat (chloramphenicol acetyl transferase), β-gluc (β-glucuronidase), and AFOS (alkaline phosphatase). Said control elements have also been transferred to regulate the control of bacterial luciferase production in bacterial cells. For example the genetic control elements from the so-called mer operon, responding to mercury, nave been transferred from certain transposons to regulate the synthesis of *V. harveyi* luciferase (Condee and Summers, 1992, J.

Bacteriol., 174, 8094–8101). A good aspect of the control elements is their precise control, resulting in high specificity and an almost background-free operation. The said control element is, so to say, closed when no mercury is present. The method is also simple to perform, and it can be performed even in field conditions. The method for the study of elements specific for mercury, described in the said publication, has a drawback in its use of heat-sensitive and ineffective luciferase, which can also be seen in the relatively low detection sensitivity, which was in this study 10 nM for $Hg^{2+}$. Almost all bacterial luciferases are relatively sensitive to heat, and at 37° C. they are rapidly inactivated, from which there follows a reduction of the sensitivity of the method. Bacterial luciferases are also ineffective in the sense that their so-called quantum efficiency is very low. This means that only 5–10% of the theoretical maximum (100%) of the chemical energy can be made visible in a reaction catalyzed by bacterial luciferase.

Another example which can be mentioned is the method for the detection of arsenic and cadmium, in which an operon responding to the said metals was placed to regulate V. harveyi luciferase genes. The said plasmid construction was capable of operating in both E. coli and S. aureus, enabling the effect of the metals to be monitored on the basis of luminescence in two different organisms (Corbisier et al., 1993, FEMS Microbiol. Lett., 110, 231–238). The sensitivity of the method to cadmium was 0.5 µM and to arsenite ion 0.1 µM. The different heavy metals have effect in this test at different speeds, owing to the variability of the mechanism of action of the factors and on the heavy-metal element used. The drawbacks of this method are the same as those described for the mercury determination above. The bacteria used in the test must be capable of measuring even picomolar heavy-metal concentrations, depending on the compound assayed.

For the reasons stated above, the described heavy-metal determination method utilizing bioluminescence-based cloned strains which contain a luciferase gene of bacterial origin cannot be easily applied to the assaying of environmental waters. Serum and urine may also be problematic targets of determination.

It is to be noted that a number of elements responding to organic compounds of heavy metals exist in nature, and some of them have also been isolated and their base sequences have been determined (see Table I).

It is also to be noted that often the bacteria used are not capable of producing a transport mechanism specific for each heavy metal, in which case the bacterium concerned is not sensitive for biosensor applications. This factor makes determination problematic, but it can be eliminated by transferring, by genetic engineering techniques, the transport mechanism of the metal concerned into the cell to be used as a biosensor.

TABLE I

Certain control elements responding to heavy metals, and their literature references.

| Heavy metal | Abbreviation | Isolated from | Base sequence | Reference |
|---|---|---|---|---|
| $Hg^{++}$ | merR | Tn21 | + | NiBhriain et al. |
| $Hg^{++}$ | merR | Tn501 | + | Misra et al. |
| $Hg^{++}$ | merR | pDU1358 | + | Griffin et al. |
| Arsenite | arsR | E. coli | + | Wu and Rosen |
| $Cu^{++}$ | pcoR | E. coli | + | Rouch |
| Chromate | chrB | A. eutrophus | – | Nies et al. |

TABLE I-continued

Certain control elements responding to heavy metals, and their literature references.

| Heavy metal | Abbreviation | Isolated from | Base sequence | Reference |
|---|---|---|---|---|
| Cadmium | czcR | A. eutrophus | + | Nies |
| Silver | — | P. stuzeri | – | Haefeli et al. |

References:

Griffin, H.G., Foster, T. J., Silver, S. and Misra, T. K. (1987) Proc. Natl. Acad. Sci. USA, 84, 3112–3116.

NiBhriain, N., Silver, S., and Foster, T. J. (1983) J. Bacteriol., 155, 690–703.

Misra, T. K., Brown, N. L., Fritzinger, D., Pridmore, R., Barnes, W., and Silver, S. (1984) Proc. Natl. Acad. Sci USA, 84, 5975–5979.

Wu, J. H. and Rosen, B. P. (1991) Mol. Microbiol., 5, 1331–1336.

Rouch, D. A. (1986) Plasmid-mediated copper resistance in E. coli. Ph.D. Thesis, The University of Melbourne.

Nies, A., Nies, D. H., and Silver, S. (1990) J. Biol. Chem., 265, 5648–5653.

Haefeli, C., C. Franklin and K. Hardy (1984) J. Bacteriol., 158, 389–392

Nies, D. H. (1992) J. Bacteriol., 174, 8102–8110.

Besides bacterial luciferases, there are known a number of eucaryotic enzymes which are capable of producing light in catalysis. The best known of these is firefly luciferase, which may be derived from a number of different species, such as Photinus pyralisi, Luciola minengrelica, Luciola cruciata, etc. In addition, luciferases using similar chemistry have been isolated from beatles, such as Pyrophorus plagiophthalamus, and from the glowworm, Lampyris noctiluca (Campbell, Chemiluminescence, 1988, Ellis Horwood Ltd, Chichester). The quantum efficiency of firefly luciferase is very high, over 80%. The reaction catalyzed by insect luciferase is as follows:

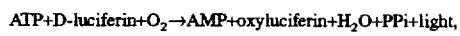

where the adenosine triphosphate reacts with a substance called D-luciferin and oxygen, whereby the corresponding oxidation products, inorganic pyrophosphate and light are formed. The wavelength of the light formed is in general within the range 540–620 nm, whereas in the case of bacterial luciferase it is 470–520 nm. Most of the genes coding for these luciferases have been cloned and sequenced and been expressed in pro- and eucaryotic organisms (Lampinen et al., 1992, Mol. Gen. Genet., 232, 498–504; Karp et al., 1992, Bio/Technology, 10, 565–569; DeWet et al., 1987, Mol. Cell. Biol., 7, 725–737). Production of light, in vivo, can be achieved by adding D-luciferin from outside the cell, and if it is desired to have the bioluminescence to be almost proportional to the intracellular luciferase content, the external pH of the cell is lowered to a pH value close to 5.0, whereupon the D-luciferin protonates and passes with considerable ease through the cell membrane. The said factors make these luciferases highly usable tools as various reporter molecules. It is conceivable that a luciferase producing one wavelength will serve as an indicator of the general condition of the cell and a luciferase producing another wavelength will report specifically on a certain event in the cell or in its external state. Such a test arrangement can easily be organized by means of apparatus technology.

Other eucaryotic luciferases include aequorines, which are produced by a jellyfish called *Aequorea victoria*. Aequorine produces light when it reacts with $Ca^{2+}$ ions, and its quantum efficiency is also very high. The color of the light produced is blue, the wavelength maximum being approx. 470 nm. However, the light emitted by the jellyfish is green, since the light emitted by aequorine excites another protein in the jellyfish, a green fluorescent protein (GFP), which turns this energy into green light in vivo (J. G. Morin and J. W. Hastings, 1971, J. Cell. Physiol. 77, 313). The gene coding for the said protein has been cloned (Prasher et al., 1992, Gene, 111, 229–233), and its nucleotide sequence has been determined. As a specialized application, GFP has been suggested as a useful marker for gene expression, since it has been observed that the protein fluoresces also in other organisms which have been transformed by genetic engineering with a gene coding for GFP (Chalfie et al., 1994, Science, 263, 802–805). In these cases the transformed cell can be caused to fluoresce when it is excited with blue light (450–490 nm). The luciferase of shrimp, *Vargula hilgendorfii*, has also been cloned and sequenced, as well as been expressed in eucaryotic cells (Thompson et al., 1989, Proc. Natl. Acad. Sci. USA, 86, 6567–6571). In addition to the above, also certain fishes and other marine creatures can produce light, with a high quantum efficiency (additional information can be found in Campbell's excellent book, Chemiluminescence). Firefly luciferase has been used as a highly sensitive meter of the ATP amount, capable of measuring molar contents as low as $10^{14}$. An application of this is a sensitive measuring of contaminating bacterial amounts in, for example, foods, since the ATP content is almost constant in a living cell.

The need for a rapid and simple determination of heavy metals, toxins and additives of foodstuffs is great. At present, the determinations usually have to be performed in a centralized manner in large laboratories, since the apparatuses (e.g. atom absorption spectrophotometer) are very expensive and require the user to have specialized training. Rapid qualitative and also quantitative tests could, performed on site, also constitute a significant screen for samples requiring further analysis. Thereby the load on laboratories would be reduced and the analysis of problem samples would be speeded up. Also, many samples suffer from the delay between the sample taking and the analysis. Determinations of heavy metals are performed on various environmental, industrial-process and contaminated waters, on body liquids such as urine, blood and serum, on saliva and hair, on foodstuffs such as canned meat, fish and raw materials.

Genetic engineering has enabled bacteria and yeasts to be used as production organisms even for proteins not normally produced by these microbes. For these purposes, various recombinant DNA plasmids have been prepared which are extra-chromosomal ring-like DNA molecules much shorter than a chromosome.

Recombinant DNA plasmids, in which the production of a foreign, recombinant protein has been placed under the control of a strong promoter, have been developed in large numbers in recent years. In all cases the aim has been to achieve a maximally high production of a foreign protein in new producer organisms such as *E. coli*. In these cases the desired protein can be produced in an amount up to 25% of the total protein of the bacterium (Caulcott & Rhodes, 1986, Trends in Biotech., June, 142–146). When such large amounts of a foreign protein are produced it is highly probable that this production is detrimental for the bacterium and its metabolism. In terms of the detrimental effect, plasmids have been developed in which the production of a foreign protein has been placed under the control of a regulatable promoter. In this case the production of protein can be switched on at a desired stage of growth of the microbe. In these cases the culturing is carried out in conditions non-stressing on the microbe for a sufficiently long period, until the microbial growth reaches a suitable cell density. Thereafter the production of the desired protein is switched on, for example, by adding a chemical switching molecule to the culture solution, or the switching is carried out by physical means, such as raising of the temperature.

The copy number of plasmids is often very different, varying from one to several hundred, up to a thousand. The copy number of the most commonly used plasmid pBR322 is approx. 60, whereas the copy number of its derivative pUC8 is approx. 500. It has been shown that this great a copy number change between two related plasmids is due to the change of one base within the so-called ori region (Chambers et al., 1988, GENE, 68, 139–149). By affecting the initiation of plasmid replication by placing this ori region under the control of a strong and regulatable promoter it is possible artificially to increase the plasmid copy number in a desired manner at a suitably selected time. At present, several plasmids are known the copy numbers of which can be changed in the course of microbial growth. These plasmids are used primarily in industrial processes to produce considerable amounts of foreign recombinant proteins. Thus the use up to now does not exclude the methods described in the present invention of using a copy number change for measuring various factors affecting a cell, such as the presence and concentrations of heavy metals. The present invention uses as an example a runaway plasmid in which a change of the copy number is possible.

The most researched and used plasmids for the production of foreign proteins are the plasmids of the so-called pOU series, in which the factors regulating the initiation site of plasmid replication are placed under the control of a strong and regulatable lambda phage $P_R$ promoter (Larsen et al., 1984, GENE, 28, 45–54). The lambda PR promoter is controlled by repressor protein c1857, which can be destroyed by a 42° C. heat treatment. Repressor protein can be produced from a lysogenic phage, a phage conjugated to the chromosome of the host organism, a plasmid to which a sequence coding for the said protein has been transferred, or from another plasmid belonging to a different incompatibility class. By an incompatibility class is meant here a case in which the presence of one plasmid in the same cell will not disturb the activity of another, different plasmid or its division into daughter cells in connection with cell division. When the control protein has been destroyed, the $P_R$ promoter switches on and begins to produce, in an uncontrolled manner, copB and repA proteins derived from a low copy number R1 plasmid, as well as their transcription products and transcription products corresponding to copA genes. These factors, and especially a vigorous overproduction of repA protein, will cause an increased and even uncontrolled production of a pOU-based plasmid in *E. coli* bacteria.

The present invention describes a method in which the lambda phage control system is replaced by a heavy-metal control unit, from which there follows dependence of the copy number of the plasmid on the amount of heavy metal present, which further leads to the amplification of the marker protein and an ultra-sensitive heavy metal determination.

Four different recombinant DNA vector types have been distinguished in yeasts; integrating plasmids (YIp), episomal plasmids (YEp), replicating plasmids (YRp), and artificial chromosomes. The integrating plasmids of yeast contain DNA of bacterial origin and a portion of a yeast gene. This plasmid type binds precisely to a certain site in the chromosomal DNA of a yeast cell. The replicating plasmids of yeast contain DNA of bacterial origin, a portion of a yeast gene, and a specific region of the chromosomal DNA of yeast, which contains the initiation site of the replication of the said plasmid. This region which regulates replication allows the division of the plasmid as an extra-chromosomal DNA molecule in the yeast cell. The episomal plasmids of yeast contain a DNA sequence of bacterial origin, a yeast cell gene, and a whole so-called 2-micron plasmid of yeast, or a portion thereof (Hollenberg, 1982, Current Topics in Microbiology and Immunology, 96, 119–144).

The use of higher eucaryotic cells as host cells for recombinant DNA vectors when it is desired to produce proteins is a rapidly developing field. The general principle in the developing of expression systems is that, by means thereof, the desired eucaryotic proteins could be produced on a large scale. By means of an optimal expression system it would be possible to produce proteins in a plurality of different cell types. A completely controllable protein expression system would be ideal in a number of different cases.

It is possible to regulate gene expression in eucaryotic cells in, for example, the following manners: by means of Simian virus 40 (SV40) T-antigen, metallothioneine genes, heat-shock genes, glucocorticoidal hormones, DNA methylation, and anti-sense RNA. The antigen produced by SV40 regulates its own transcription. T-antigen is produced in large amounts immediately after the virus has infected its target cell, and later T-antigen binds to its own promoter sequence and inhibits transcription. When SV40 vectors are used for clonings, this T-antigen mediated regulatory function can be inhibited by using a suitable heat-sensitive T-antigen mutant. Such heat-sensitive T-antigen mutants normally produce T-antigen at high incubation temperatures, whereas at room temperature the production of T-antigen is inhibited (Rio, D. C., Clark, S. G. & Tjian, R., 1985, Science 227, 23–28).

Metallothioneines and sideophores are proteins which bind heavy metals. Many eucaryotic cells begin to produce these proteins in the presence of heavy metals. Bacteria produce sideophores for binding metal ions outside the cell. A 50-fold increase in the production of metallothioneines was observed when cadmium was added to a cell culture solution ad $4\times10^6$-molar concentration (Hamer, D. H. & Walling, M. J., 1982, J. Mol. Appl. Genet., 1, 273–288). The above-mentioned cadmium-induced protein production can be further increased by using culture solutions which contain a minimal amount of heavy metals.

The present invention utilizes bacterial cells prepared by the recombinant DNA technique, the cells being suitably selected strains and containing the appropriate recombinant DNA vector constructions. The invention uses luciferase-coding, genes derived from insects, the genes being regulated by genetic elements responding to heavy metals. These elements can be isolated from either procaryotes or eucaryotes. Insect luciferases are stable at physiological temperatures (37° C.), and their quantum efficiency is 88%; these factors in the main affect the functioning of the test. In addition, genetic elements which regulate the synthesis of marker protein contain nothing but, and only a minimal amount of, genetic information which is needed for regulating the expression of the marker protein.

For the determination of compounds to be analyzed it is possible to prepare different recombinant DNA vector constructions, depending on what the heavy metal compound to be determined is. For example, an element responding to mercury may be placed to regulate the value of the plasmid copy number and simultaneously the activity of the insect luciferase gene in the plasmid. By this procedure, an immense replication effect is achieved when mercury is present, and the amount of mercury can be correlated by means of luciferase activity measurements. In a measurement of this kind the result is obtained in a couple of hours.

In a special rapid application, the luciferase gene may be located under the control of an element responding to heavy metals in a plasmid having a constant copy number. Thereby the determination is made more rapid, and it may yield information about the surrounding heavy metal contamination in as few as ten minutes. In this case the sensitivity of the method is, of course, limited, but it is sufficient for measuring heavy metal contamination in environmental waters.

The character of the invention makes highly different measuring methods possible. The advantage of luciferase measurement is the sensitivity of the measuring of light as compared with, for example, spectrophotometric determinations. The use of a simple black box in which an X-ray film is exposed is well-founded in cases in which sensitivity is not the most important criterion but rather the simplicity and speed of the method. A portable, relatively sensitive luminometer equipped with a photomultiplier tube or a light diode, of which an avalanche photomultiplier can be mentioned as a special case, is well-founded in those cases in which the determination must be made in field conditions. A luminometer which reads microtiter plates is needed when the number of samples is very high. A so-called Doctor's Office device could be regarded as a special case; it could be used, for example, in a dentist's office for measuring the amount of mercury dissolving from amalgam fillings. The most important advantage of this method is the use of non-dividing cells, the result being a very rapid determination, even less than half an hour.

The invention is described in detail with reference to figures.

FIG. 1 depicts a diagram for sensitive demonstration of heavy metal from a biological or non-biological material by a method which is based on the increasing of the copy number of a plasmid in the presence of a heavy metal, an element responding to heavy metals regulating the copy number of the plasmid. For the sake of clarity, a considerable number of factors have been left undepicted in the figure, these factors affecting the activity of the cell and the recombinant plasmid and being generally known facts. The cell shown in the figure is depicted as a two-membrane microbial cell. It could just as well be a single-membrane microbial cell or eucaryotic cell. The heavy-metal responding element, depicted as a black ball in the initial situation, controls the synthesis of units responsible for the plasmid copy number (called COP in the figure). The luciferase gene (LUC) in the same plasmid is controlled by the same or some other control unit, which is depicted as a black square. In the presence of the heavy metal to which the said control element is sensitive, a change in conformation occurs in the regulator protein (depicted as a partial opening of the black ball), an uncontrolled increase of the plasmid copy number starts immediately, the increase being shown in the following picture as an increase in the number of small balls. When the synthesis of luciferase is initiated (for example, induced from the inducing control unit, depicted as partial opening of the black square) i.e. the promoter, the cell first begins to produce messenger RNA (depicted as undulating lines in the subsequent picture), and thereafter a specific globular luciferase enzyme (depicted as bundles of thread). When luciferase is added, the luciferase protein produces light and thereby makes the cell bioluminesce, which phenomenon can be measured and the amount of which correlates directly with the amount of heavy metal used. For the sake of clarity, different stages have been drawn in the figure; in practice, however, the determination can, when so desired, be performed with all the different stages occurring simultaneously.

FIG. 2 depicts a diagram for sensitive demonstration of a heavy metal in a biological or non-biological material by a method which is based on direct enzyme induction from an element responding to the heavy metal. For the sake of clarity, a considerable proportion of factors which affect the activity of the cell and the recombinant plasmid and which are generally known facts have been left out of the picture. The cell in the figure is depicted as a two-membrane microbial cell. It could just as well be a single-membrane microbial cell or eucaryotic cell. In the initial situation, the heavy-metal responding element (depicted as a black ball) in the cell, placed to regulate luciferase (LUC) synthesis in the recombinant vector (depicted as a thick arrow), is very precisely switched off, and no messenger RNA is being produced from it. In the subsequent stage, when heavy metal to which the said control element is sensitive is added to the extra-cellular solution (the heavy metal passes to inside the cell via group-specific ion-transport channels), a change in conformation (depicted as partial opening of the black ball) occurs in the regulating protein, transcription starts immediately (depicted as undulating lines), as also does the corresponding synthesis of luciferase protein (depicted as bundles of thread, which represent globular luciferase proteins). When luciferin is added, the luciferase protein produces light and thereby makes the cell bioluminesce, which phenomenon can be measured and the quantity of which correlates directly with the quantity of the heavy metal used. For the sake of clarity, different stages have been drawn in the figure; in practice, however, the determination can be carried out, when so desired, with all the different stages occurring simultaneously.

Figure 1:
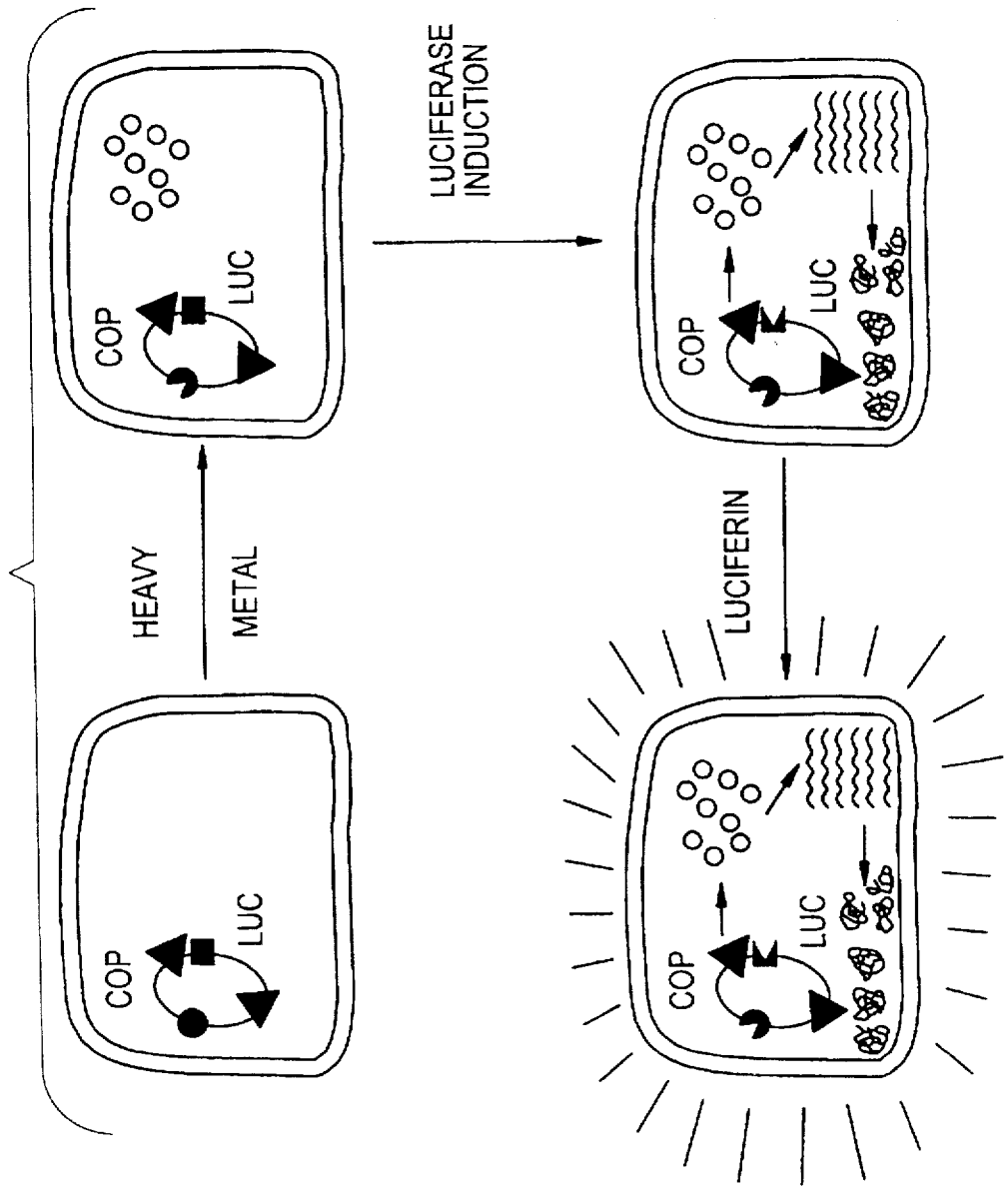
Figure 2:
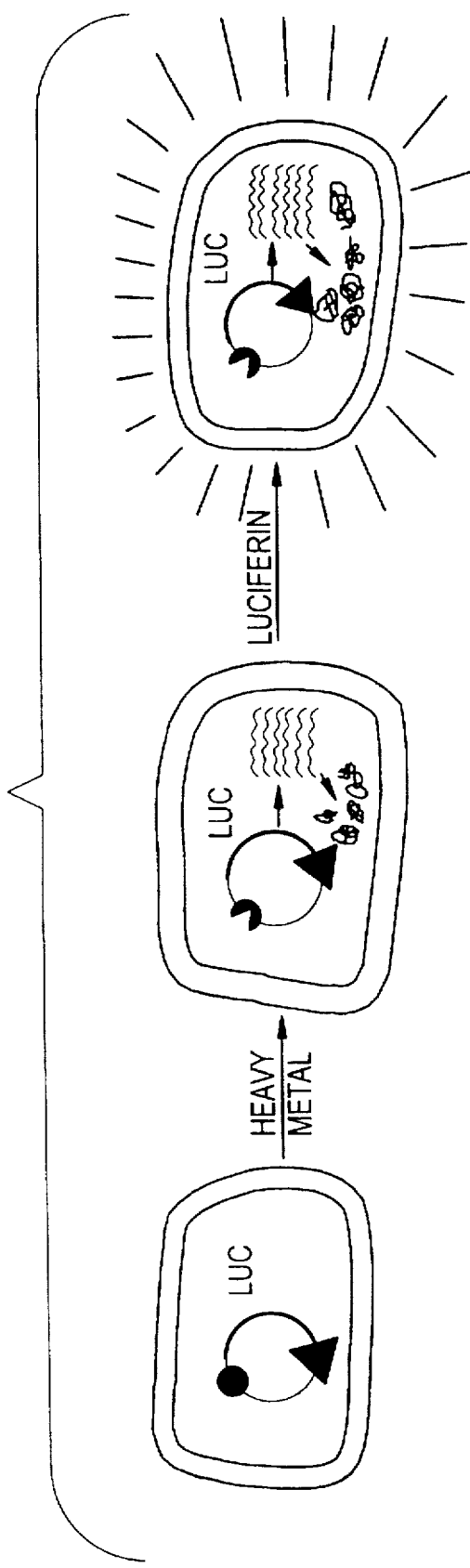

It is to be noted that the method starts from a few luciferase molecules, more of which can be produced at a desired time without it being in any way dependent on the division of the cell itself. This enables even undivided cells to be used for testing for heavy metals, in which case the time taken by the determination is not limited by slow division of the cells. Thus this also makes heavy metal determinations elsewhere than at a laboratory possible. In this case a determination can be carried out, for example, in the office of a school health nurse, if it is desired to determine the concentration of lead in children's blood. Likewise, a determination can be performed at an industrial waste water precipitation basin by using a portable luminometer and a determination reagent packed in disposable tubes.

The inventional character of the present invention is based on its extreme flexibility; the methods can be applied to highly different measuring sites or sample materials—their common factor is sensitive, rapid and inexpensive detection.

It is also to be noted that by a method such as this it is also possible to monitor emissions continuously, for example from process waters of the mining industry, in such a manner that a report on a caused elevated level will automatically go to the process control room. This is possible to achieve by placing cells attached to a solid carrier in a cartridge through which there is arranged an intermittent flow of process water and luciferase reaction substrate. When cells having a constitutive luciferase expression are bound to a control cartridge, these cells indicating the condition of the cells and thus the time when the cartridge must be replaced (which can also be automated), a reliable method can be developed for automatic monitoring of an industrial process. The attaching to a solid carrier can be done in a number of different ways, for example through the expression, on the surface of the same cell, of a peptide, CBDCex, binding to cellulose, the peptide being derived from a gene coding for the cellulose enzyme of *Cellulomonas filmi* (Francisco et al., 1993, Bio/Technology, 11, 491–495; Gilkes et al., 1988, J. Biol. Chem., 263, 10401–10407). The cellulase enzymes of also other organisms contain subunits, suitable for the purpose and binding to an inexpensive solid carrier, the genes coding for these subunits being expressible when fused with the surface proteins of the cell.

The invention utilizes promoters regulatable by means of heavy metals and functions regulated by these promoters. The promoters contain a region to which the RNA polymerase enzyme can bind and a region intended for the binding of a special control protein or other molecule. By promoters is indeed simply meant a unit in the DNA, which unit controls the expression of a gene adjacent to or in the vicinity of the unit. Switching promoters for *E. coli* bacterium include lac, trp, hybrid promoter tac, and lambda phage $P_L$ and $P_R$ promoters. These promoters differ from each other, for example, in their strength and manner of switching. Lac and trp promoters can be switched on by means of chemical compounds, whereas the switching on of the $P_L$ promoter can be carried out simply by raising the temperature. In the present invention the promoters are switched on specifically by heavy metals.

The essential characteristics of the invention are stated in the accompanying patent claims.

The invention is described below in greater detail with the help of examples.

EXAMPLE 1

Cell strains, plasmids and their construction and methods used in the invention

*E. coli* MC1061 (Casadaban and Cohen, J. Mol. Biol., 138, 1980, 179–207) were used as gene transfer hosts and in toxicity tests. The cells were cultured on appropriate minimal plates, and the plates were stored at maximum for 1 week at +4° C., whereafter the bacteria were transplanted to new plates. The strains were also stored at –70° C. in 15% glycerol, from which, when necessary, culture on a minimal plate was started. For plasmid isolation, cells were first cultured in a volume of 5 ml (2×TY medium, described below) for 10 hours at 30° C. under shaking, and the initial culture was transferred to a larger volume of the same medium for 10 hours.

Treatment of *E. coli* strains for the transfer of recombinant DNA plasmids

Recombinant DNA plasmids were transferred into so-called $CaCl_2$-treated cells so that cells cultured overnight were rejuvenated by transferring a 5 ml culture in 2×TY (NaCl 8 g, yeast extract 8 g, and trypton 16 g, $H_2O$ ad 1 l, pH 7.4) to 100 ml of the same liquid. The cells were cultured for approx. 2 hours, until the absorbance measured at 600 nm was 0.8. The cells were cooled in an ice bath and were centrifuged down at 4000×g, 5 min. The cell pellet was suspended in 50 ml of 50 mM $CaCl_2$ in an ice bath, followed by centrifugation down at 3000g, 5 min at 0° C. The cells were suspended in 4 ml of 50 mM $CaCl_2$, to which glycerol has been added ad 15%. In this case these so-called competent cells were divided into 1 ml aliquots, were cooled rapidly in liquid nitrogen, and were stored at –70° C. for later use.

Transformation of *E. coli* strains with recombinant DNA plasmids

250 µl of either fresh or frozen competent cells were added into tubes already cooled in an ice bath and containing 1–10 µl of a pure plasmid DNA or a so-called ligation mix and 26 µl of 10×TMC (100 mM Tris-Cl, pH 7.4, 100 mM $MgCl_2$). The mixture was stirred gently and was kept in an ice bath for 10 min (frozen cells) or 60 min (fresh cells). In some cases the cells were thereafter kept at 42° C. for 2 min under shaking. Thereafter 1 ml of 2×TY liquid was added and the tubes were shaken for 1 hour at 30° C. The cells transformed by using ligation mixes were centrifuged down for 3 min at 4000×g, were suspended in approx. 100 µl of centrifuged supernatant, and were applied to antibiotic selection plates. Of the transformed cells which contained pure plasmid DNA, a suitable amount was directly applied to antibiotic plates.

Determination of the gene sequence of double-stranded DNA

Approx. 4 µg of a double-stranded DNA purified by standard methods (e.g. CsCl gradient) are added to 2 µl of 2 M NaOH. The mixture is allowed to stand for 5 min at room temperature, and 3 µl of 3M Na acetate, pH 4.5, and 2 µl of $H_2O$ are added. The DNA is precipitated by adding 75 µl of absolute ethanol, and the mixture is allowed to stand for 30 min at –70° C. The precipitated DNA is centrifuged down for 5 min at 12000 rpm in an Eppendorf microcentrifuge and is washed once with 70% ethanol. After the centrifugation, the precipitate is dried for 5 min in a vacuum desiccator, and after the drying the precipitate is dissolved in 4 µl of water. Simultaneously 5 pmol of a specific primer and 1 µl of 10×Klenow buffer (composition described in the sequencing guide book of Amersham, Ltd) were added. From the dissolving on, the procedures are performed at 37° C. The mixture is allowed to stand for 15 min, whereafter 1 unit of Klenow enzyme, 4 µl of $^{35}$S labeled deoxy-ATP (500 µCi/ml) are added, and mixing is performed by centrifugation. 3.5 µl of the above mixture is taken into each of the dideoxynucleotide reaction tubes (the proportions of deoxy- and dideoxynucleotides are described in the guide book) and is allowed to stand for 15 min. To each of the four tubes, 1.5 µl of Chase solution is added, in which the concentration of each deoxynucleotide is 10 mM. The tubes are allowed to stand for 15 min, whereafter the reactions are run onto a polyacrylamide gel, as described in the guide book. The gel is run according to need, whereafter the gel is fixed, dried and exposed using X-ray film in accordance with general principles.

EXAMPLE 2

Figure 3:
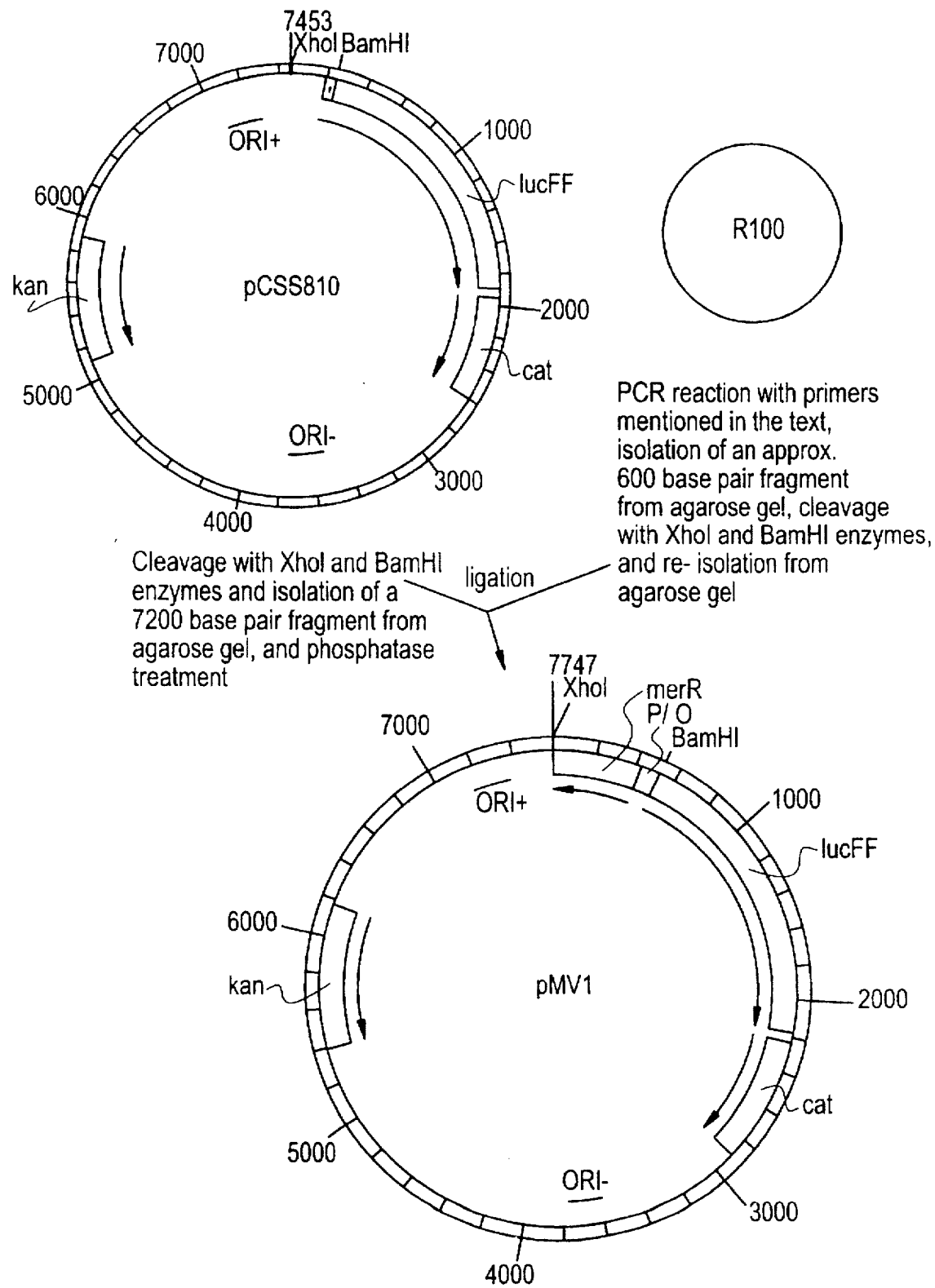
FIG. 3 shows the construction and structure of the plasmid pMV1.

Construction and structure of the plasmid pMV1 (FIG. 3)

The plasmid pMV1 described in the invention was constructed by utilizing previously described recombinant DNA plasmids and generally known molecular biology techniques. The plasmid pCSS810 was cleaved with restriction enzymes XhoI and BamHI overnight at 37° C. The cut plasmid was treated for the removal of the terminal phosphate groups by adding 0.1 unit of bovine intestinal alkaline phosphatase, and was kept at 37° C. for 30 min. The plasmid was separated from the uncut products by driving 0.8% low gelling temperature (LGT) agarose gel. Thereafter a 7300 base pair fragment was separated from the gel by cutting it in ultraviolet light. The obtained gel fragment was melted at 65° C., and the cut plasmid was isolated from it and was ligated by means of ligase enzyme to a PCR product cleaved with the same restriction enzymes. The said polymerase chain reaction product was obtained when the merR gene and the control region of mer operon were isolated by means of a PCR reaction (polymerase chain reaction) from a plasmid isolated from an *E. coli* strain (NCTC 50278). Primers of the following kinds were used in the reaction: 5'-CTTAAGGATCCCCTCATAGTTAATTTCTCCTCTT-TTGAATTTGGATTGGATA-3' SEQ ID No:1 and 5'-CAT-ATCTCGAGCTAAGGCATAGCTGACCT-3' SEQ ID No:2, as well as Taq polymerase. After the reaction, a reaction product of 550 base pairs was isolated from agarose gel, was cleaved with BamHI and XhoI enzymes, and was separated from the uncut products in the same way as pCSS810 above. These DNA fragments were combined by means of ligase enzyme. What is notable in this is that the merR gene and the control region of the mer operon were isolated in their entirety without taking along any parts unnecessary in terms of control, a fact which is important for the functioning of the present invention, producing a very sensitive mercury detection.

The obtained construction was transferred in the manner described above into the *E. coli* MC1061 bacterial strain. The isolation of recombinant DNA plasmids was done on a small scale, as described (Maniatis et al., 1982, Molecular Cloning, A Laboratory Manual, Cold Spring Harbor Laboratory, Cold Spring Harbor), and the correct plasmid construction was ascertained by restriction enzyme cleav-

13 ages. The isolation of plasmids on a larger scale was carried out according to the instructions in the same manual. The plasmid pMV1 thus constructed contains sites of initiation of DNA replication originating from both a gram-positive bacterium and a gram-negative bacterium. It is thus a so-called shuttle plasmid, which can be transferred to also other gram-negative bacteria or gram-positive bacteria, for example *B. subtilis*, by a method described earlier (Contente and Dubnau, 1979, Mol. Gen. Genet., 167, 251–258). By using a plasmid construction of this type, heavy metal determination can be done in the organism in which the detection is the most sensitive possible, i.e. the metal transport mechanisms are active. The recombinant DNA plasmid pMV1 was deposited on Nov. 10, 1993 with the depository DSM under deposit number 8708.

EXAMPLE 3

Figure 4:
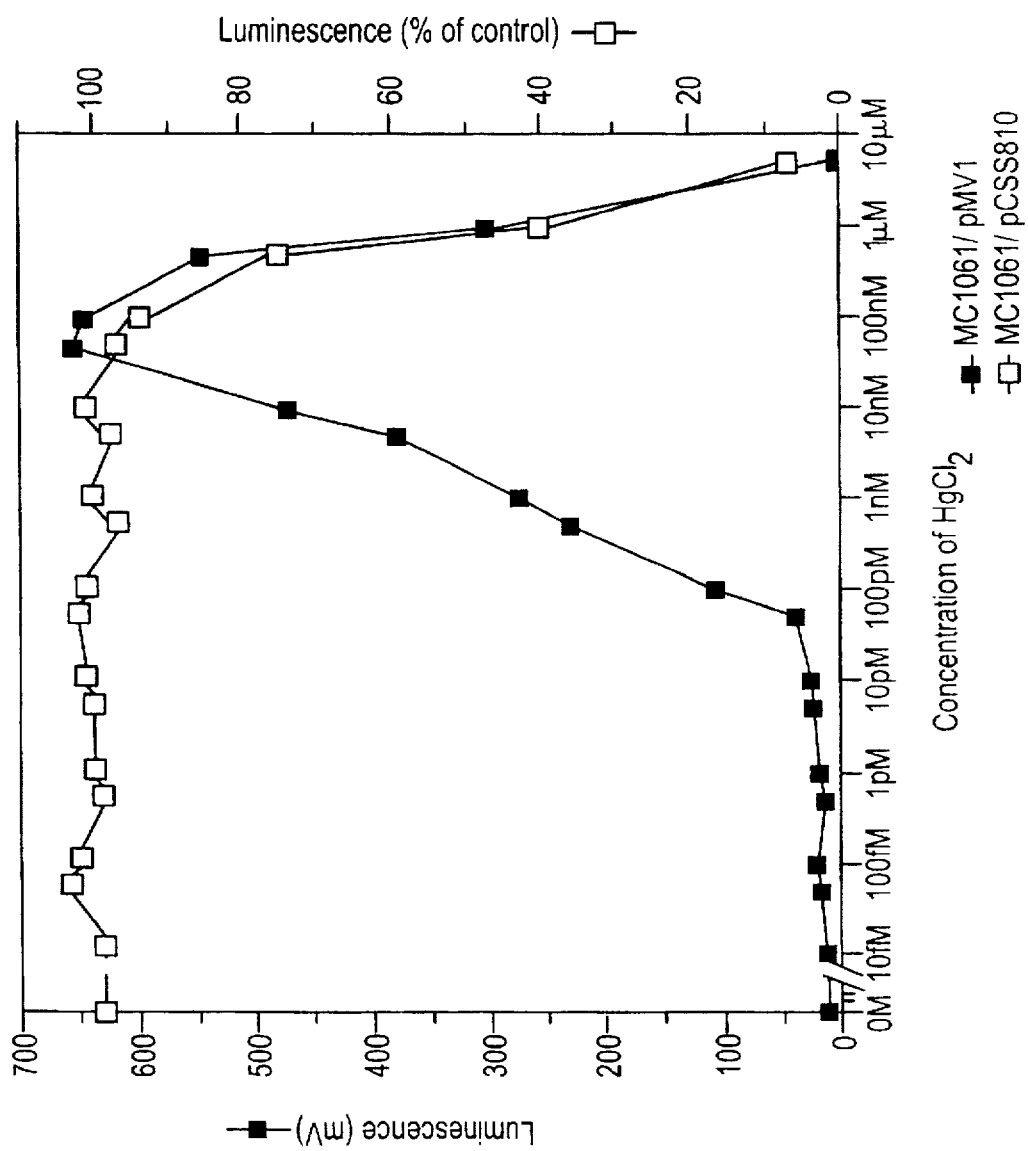
FIG. 4 depicts mercury determination based on the strain *E. coli* MC1061/pMV1, measured on the basis of luminescence: the bioluminescence of the bacteria as a function of the concentration of mercury chloride. A strain measuring general toxicity, *E. coli* MC1061/pCSS810/pGB3, is used as a control in the determination.
Figure 5:
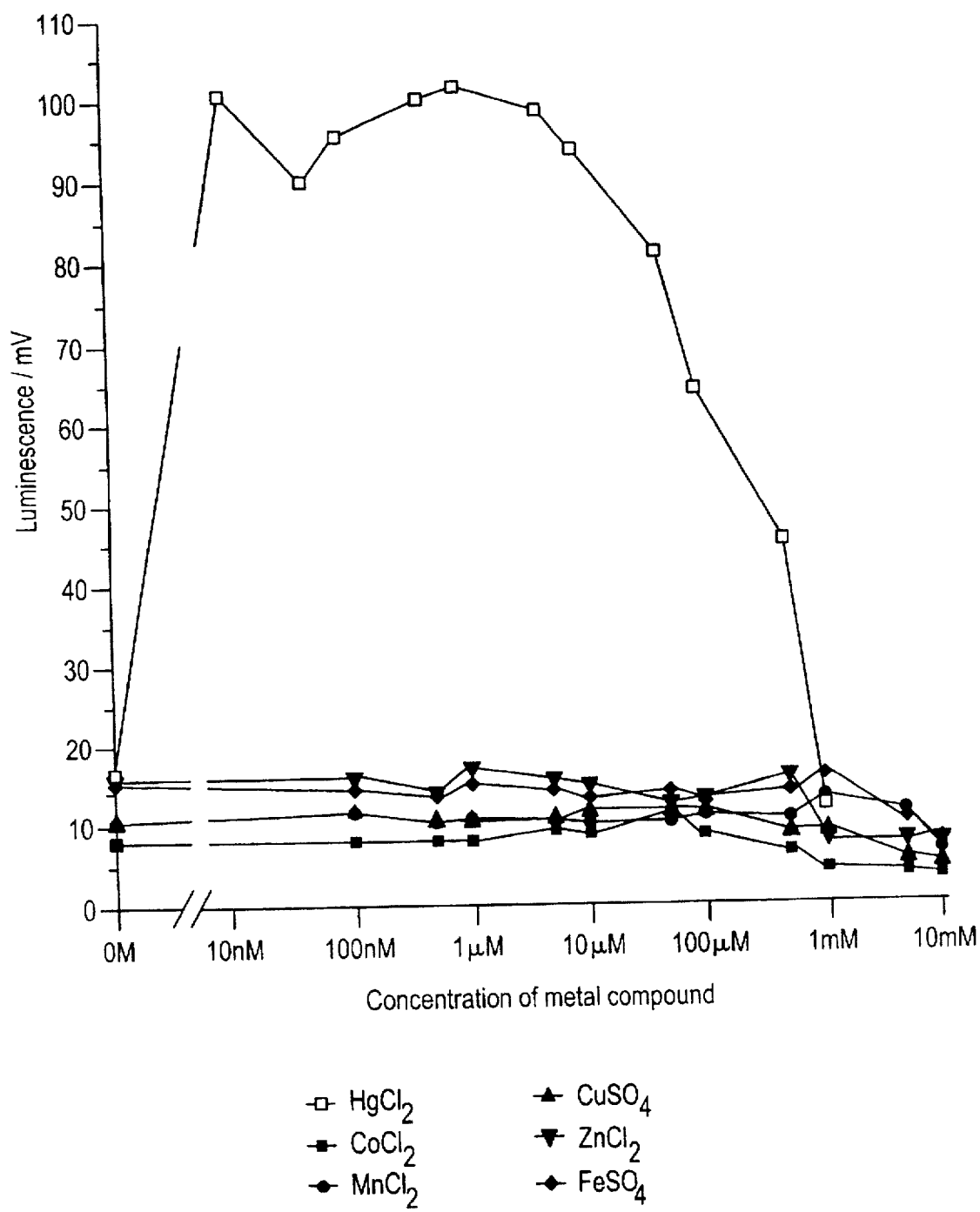
FIG. 5 depicts mercury determination based on the strain *E. coli* MC1061/pMV1, measured on the basis of luminescence: bioluminescence of the bacteria as a function of certain other metal ions.

Mercury determination based on the strain *E. coli* MC1061/pMV1, measured on the basis of luminescence Plasmid pMV1 cloned *E. coli* MC1061 cells which had grown overnight and in which $OD_{600}=1.5-2.0$ were washed twice with m9 minimal culture solution (Maniatis et al. (1982) Molecular Cloning: A Laboratory Manual, Cold Spring Harbor Laboratory, Cold Spring Harbor, N.Y.) to which acid hydrolyzed casein had been added 10 g/l. The cells were diluted 1:200 with the said culture solution. Various amounts of mercury compounds, other ion compounds, heat-treated (30 min at 56° C.) blood or water samples from the environment were mixed with these cells. The samples, which were in luminometer tubes or on a 96-recess plate were allowed to stand for 60 minutes at +30° C., whereafter 100 µl of 1 mM D-luciferin was added to the samples, and the luminescence of the samples was measured immediately. The luminescence of unknown samples was compared with the luminescence amounts induced by known mercury concentrations. The same *E. coli* cells cloned with the plasmid pCSS810 (Lampinen et al., 1992, Mol. Gen. Genet. 232, 498–504) were used as a so-called internal standard in the determination; the amount of light produced by these cells indicates the proportion of nonspecific toxicity in the surrounding liquid. FIG. 4 depicts bacterial bioluminescence as a function of the concentration of mercury chloride. FIG. 5 depicts bacterial bioluminescence as a function of certain other metal ions. It can be seen in the figure that not even high concentrations of other ions induce luminescence when the described mercury-specific biosensor is used. A corresponding determination may also be carried out by using a gram-positive bacterium, e.g. *B. subtilis*, into which the plasmid pMV1 has been transferred.

EXAMPLE 4

Determination of mercury by a method using pMV1 plasmid cloned *E. coli* cells bound to a solid alginate carrier The binding of the cells to the alginate was carried out in the following manner:

*E. coli* MC1061/pMV1 cells were cultured as in Example 2. The cells were washed twice with M9 culture solution to which acid-hydrolyzed casein had been added 10 g/l, and were suspended in the same solution. 200 µl of this solution was mixed with 2 ml of a 2% alginate solution, mixing was carried out, and the mixture was drawn into a 5 ml injection syringe. The mixture was forced through the needle into an 0.5M $CaCl_2$ solution, which was mixed with a magnetic mixer. The mixing was continued for 30 minutes, whereafter the pearls were washed with water several times and were suspended in the above-mentioned M9 solution.

Figure 6:
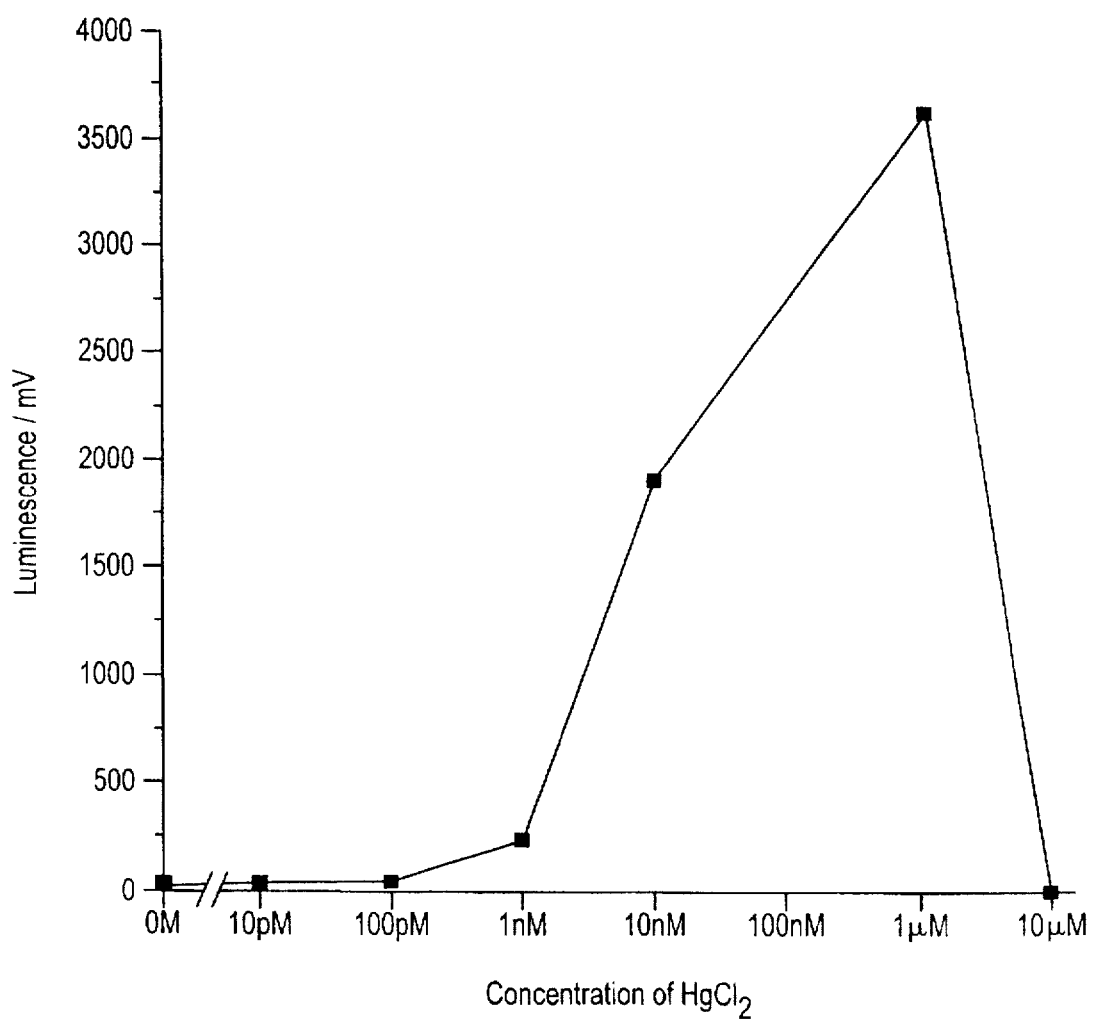
FIG. 6 depicts the determination of mercury by a method which uses *E. coli* cells cloned with pMV1 plasmid, the cells being attached to a solid alginate carrier.

FIG. 6 depicts the effect of mercury on *E. coli* MC1061/pMV1 cells bound to alginate pearls. One alginate pearl and 200 µl of M9 medium, as well as various amounts of $HgCl_2$, were added to each of the luminometer tubes. They were allowed to stand at 30° C. for one hour, whereafter the amount of light produced by the immobilized cells was measured by adding into the luminometer tubes 100 µl of 1.0 mM D-luciferin in 0.1M Na citrate buffer, pH 5.0. A Bio-Orbit 1251 luminometer was used for the determination 30 minutes after the adding of the substrate.

EXAMPLE 5

Structure and construction of the plasmid pMV2

Figure 7:
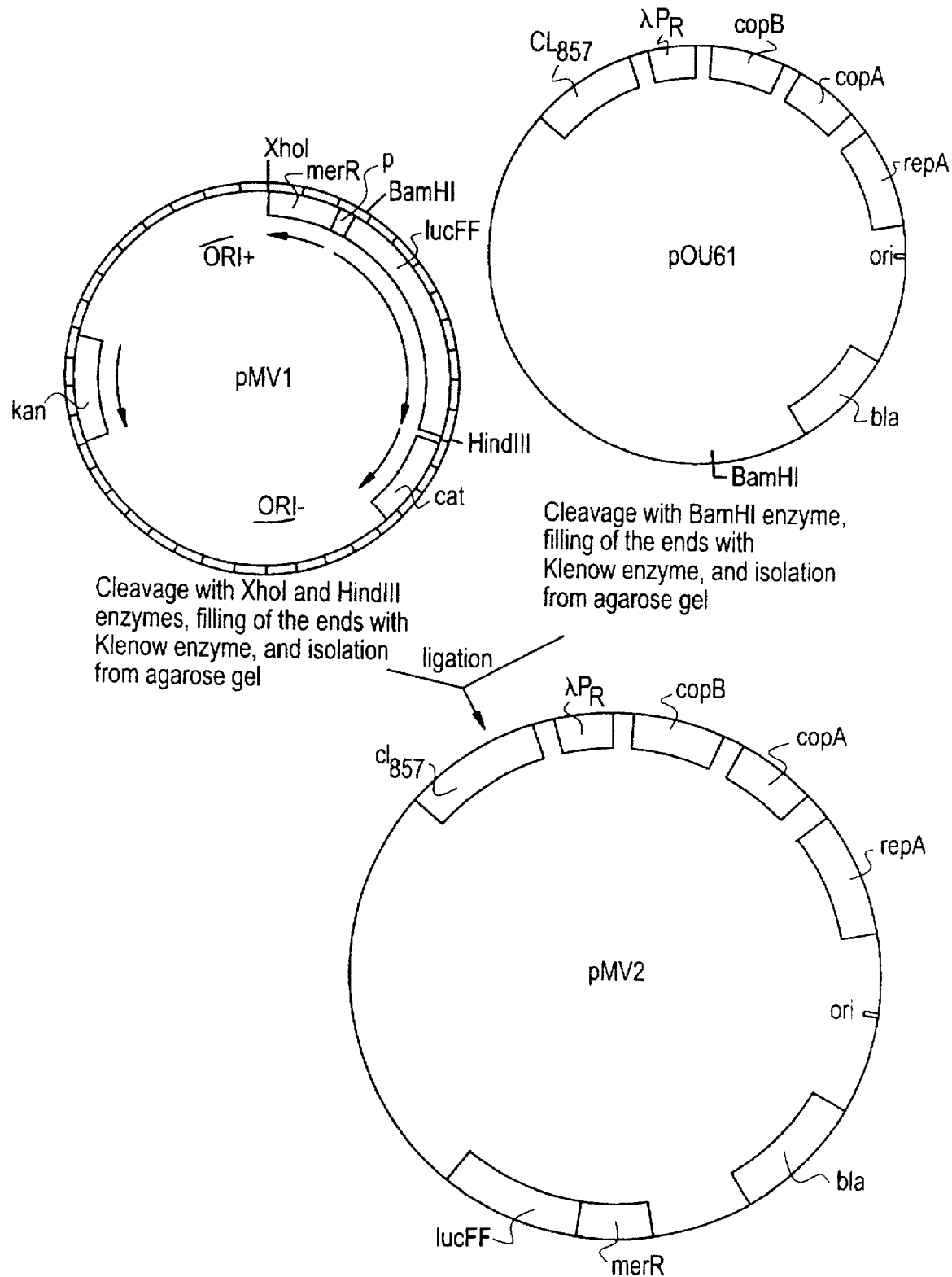
FIG. 7 depicts the structure and construction of the plasmid pMV2.
Figure 8:
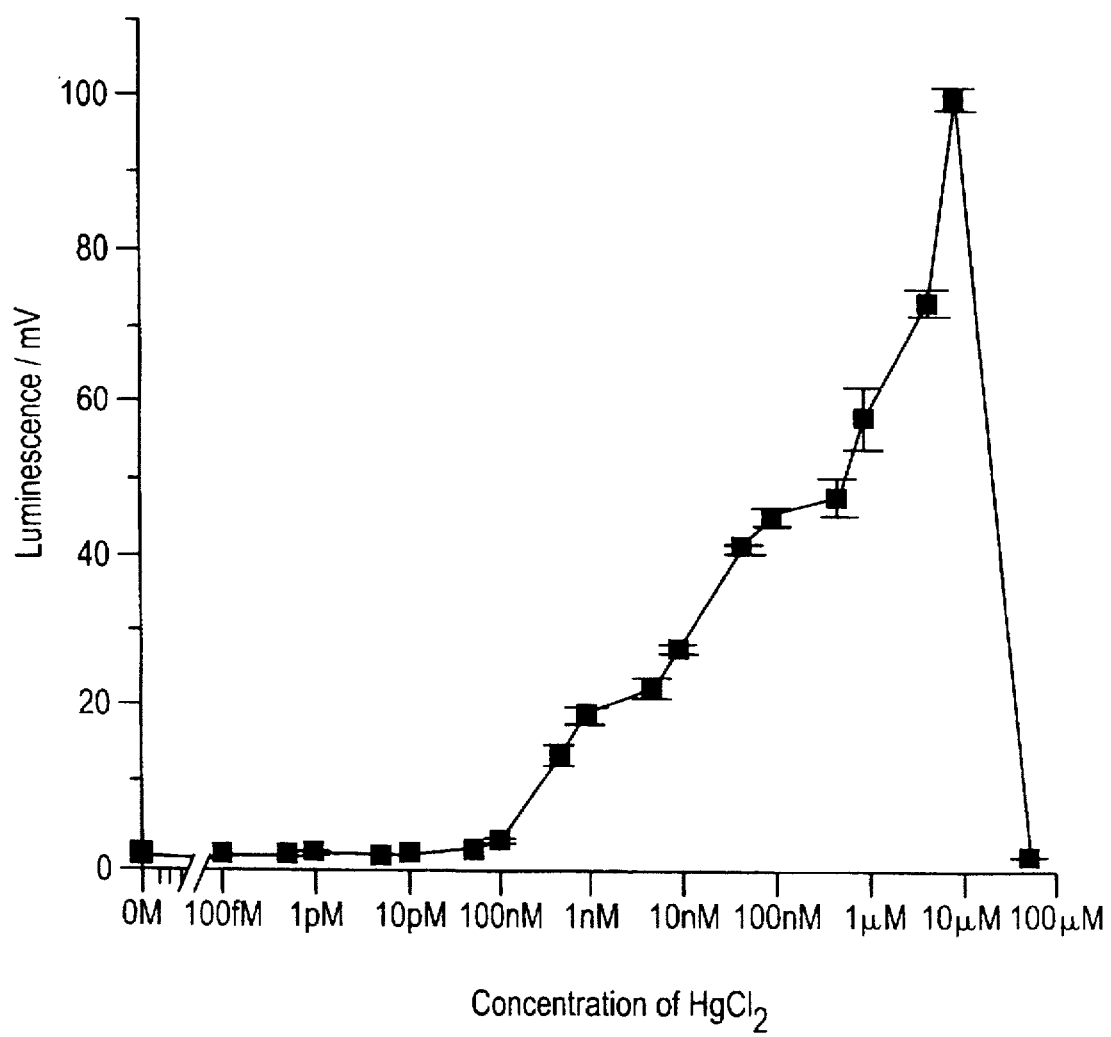
FIG. 8 depicts the determination of mercury by using an *E. coli* strain to which plasmid pMV2 has been cloned, wherein luciferase synthesis is regulated by an element responding to mercury and the copy number of the plasmid is very low.

The plasmid pMV1 was cleaved with restriction enzymes XhoI and HindIII, which detach the gene coding for firefly luciferase and the merR and mer operon regions in their entirety. The cohesive ends of the fragment were leveled out by adding deoxynucleotides ad 1 mM and 1 unit of Klenow enzyme. The reaction was maintained for 30 min at 37° C., whereafter a DNA fragment of approx. 2200 base pairs was separated with LGT agarose gel and by glass-milk treatment, as described above. The plasmid pOU61 (Larsen et al., 1984, Gene 28, pp. 45–54) was cleaved with restriction enzyme BamHI, the ends were leveled out by Klenow enzyme treatment as above. The cleaved vector DNA was treated with 0.1 unit of alkaline phosphatase to remove the terminal phosphate groups for 20 min at 37° C., and a 10 kilobase pair DNA fragment was isolated from LGT agarose gel as above. The obtained DNA fragments were ligated to each other by means of T4-DNA ligase enzyme and were transformed into *E. coli* MC1061 cells in the manner described in Example 1. Plasmid minimal plates were prepared, from which the correct structure was ascertained by restriction enzyme digestions. FIG. 7 shows the structure of the obtained plasmid pMV2. FIG. 8 shows the determination of mercury by means of an *E. coli* strain cloned with the plasmid pMV2, in which luciferase synthesis is controlled by an element responding to mercury and the plasmid copy number is very low, i.e. 1–2/cell. It is seen from the figure that the determination of mercury is almost in the same order of sensitivity as in the previous cases, and the dynamic measuring range has substantially increased to almost five decades.

EXAMPLE 6

Structure and construction of the plasmid pMV3

Figure 9:
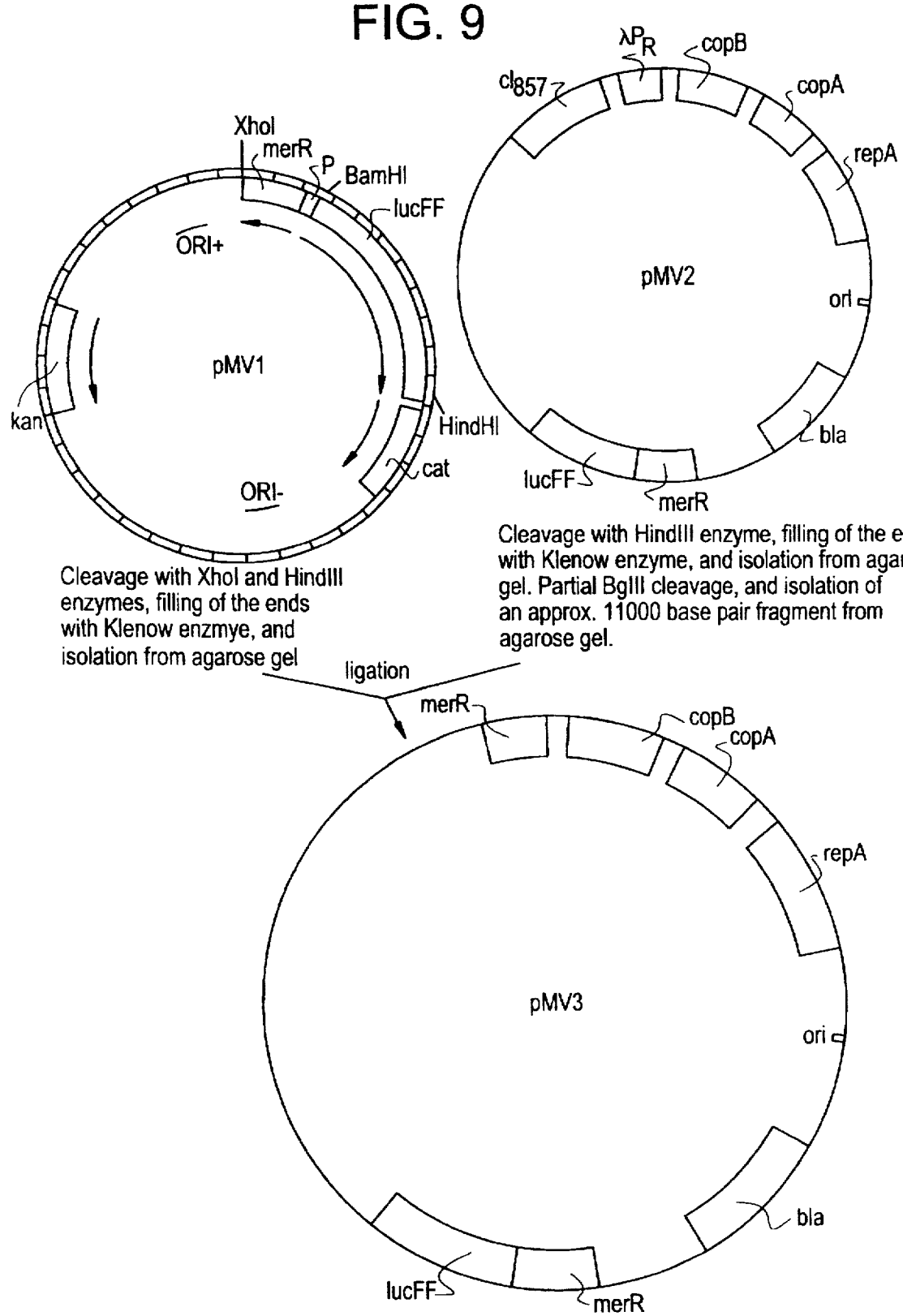
FIG. 9 depicts the structure and construction of the plasmid pMV3.

Plasmid pMV2 was cleaved with restriction enzyme HindIII, the cohesive ends were leveled out by a Klenow treatment, as above, and the enzyme was inactivated for 20 min at 65° C. Thereafter the cleaved pMV2 was cut by a partial BglII digestion and an approx. 11 kb linear vector DNA was isolated from agarose gel, as described above. To the vector thus obtained there were ligated the merR and mer operon regions from pMV1 plasmid which had been cleaved with XhoI, the ends had been leveled out with Klenow enzyme, and after heating cleaved with BamHI enzyme. The ligation was done by means of T4-DNA ligase enzyme, as above, and the mixture was transformed into *E. coli* MC1061 cells. The plasmids having the correct plasmid structure were identified by restriction enzyme digestions. FIG. 9 depicts the constructing of the plasmid. The recombinant DNA plasmid pMV3 was deposited on Jan. 10, 1994 with the depository DSM under deposit number 8893.

EXAMPLE 7

Figure 10:
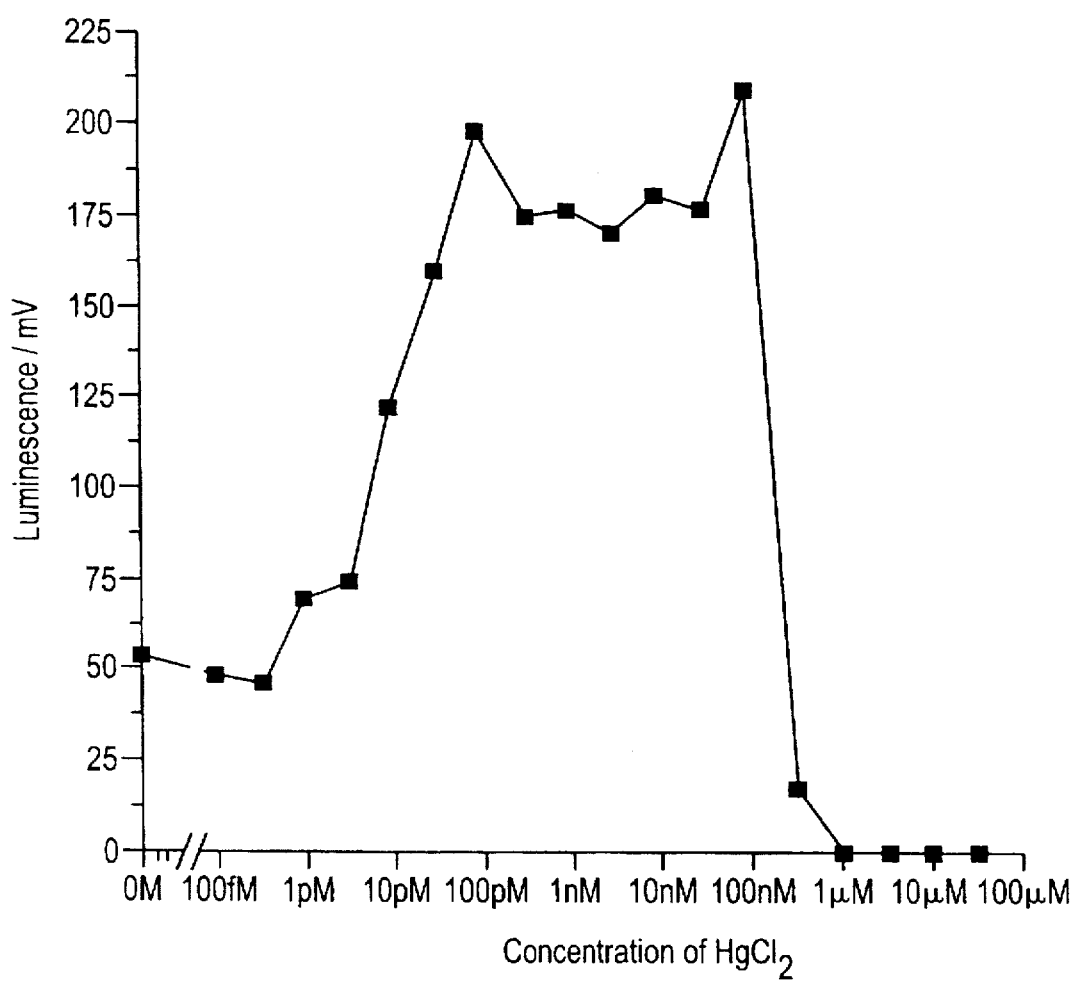
FIG. 10 depicts mercury determination based on the strain *E. coli* MC1061/pMV3, measured on the basis of luminescence.

Mercury determination based on the strain *E. coli* MC1061/pMV3, measured on the basis of luminescence Plasmid pMV3 cloned *E. Coli* MC1061 cells which had grown overnight and in which $OD_{600}=1.3-2.0$ were washed twice with M9 minimal culture solution (Maniatis et al., 1982, Molecular Cloning: A Laboratory Manual, Cold Spring Harbor Laboratory, Cold Spring Harbor, N.Y.) to which acid-hydrolyzed casein had been added 10 g/l. The cells were diluted 1:200 with the above-mentioned culture solution. Different amounts of mercury compounds were mixed with these cells. The samples, which were in luminometer tubes or on a 96-recess plate, were allowed to stand for 60 minutes at +30° C., whereafter 100 µl of 1 mM D-luciferin was added to the samples and the luminescence of the samples was measured immediately. FIG. 10 shows the bioluminescence of the bacteria as a function of the mercury concentration.

EXAMPLE 8

Construction of the plasmid PHGGFP

The plasmid pMV1 was cleaved with restriction enzymes BamHI and HinDIII and was treated with CIP enzyme to remove the terminal phosphate groups. To the vector thus cleaved there was ligated overnight at +16° C. by means of T4-DNA ligase a DNA fragment which contained the GFP gene and which had been obtained as follows: Plasmid pGFP10.1 (Chalfie et al., 1994, Science, 263, 802–805) was used as the template (10 ng) in the replication of the GFP gene by means of PCR (polymerase chain reaction). The primers used were oligonucleotides having the following nucleotide sequences (15 pmol of each): amino end primer 5'-atatggatccAGCAAAGGAGAAGAAC-3' SEQ ID No:3 and carboxy end primer 5'-aattaagcTTGGAAGTCTGGACAT-3' SEQ ID No;4. The said gene was replicated using Vent polymerase (New England Biolabs) for 25 cycles (94° C. 50 sec, 45° C. 1 min, and 72° C. 1 min) in a buffer supplied by the manufacturer, to which MG(SO$_4$)$_2$ had been added ad 2 mM, and the deoxynucleotides ad 250 µM each. The obtained PCR product was purified using LGT agarose gel, were finally dissolved in water and were ligated to the vector pMV1 in the manner described above. The ligation mix was transformed to an *E. coli* strain in the manner described above, and plasmid minimal plates were prepared of the transformants. The correctness of the obtained vector pHGGFP was ascertained from plasmid minimal plates by restriction enzyme digestions and nucleotide sequencings.

EXAMPLE 9

Mercury determination by using the strain *E. coli* MC1061/pHGGFP

The strain *E. coli* MC1061/pHGGFP with the plasmid, obtained in accordance with Example 8, was tested in the presence of various mercury concentrations. Approx. 1 million cells were incubated with different amounts of HgCl$_2$ for 1 hour at 30° C. Thereafter the amount of induced GFP was measured as described in Chalfie et al., 1994. It was observed from the results that the amount of GFP induction correlated with the extracellular mercury amount as increased fluorescence very sensitively, the detection sensitivity being at a nanomolar level.

EXAMPLE 10

Figure 11:
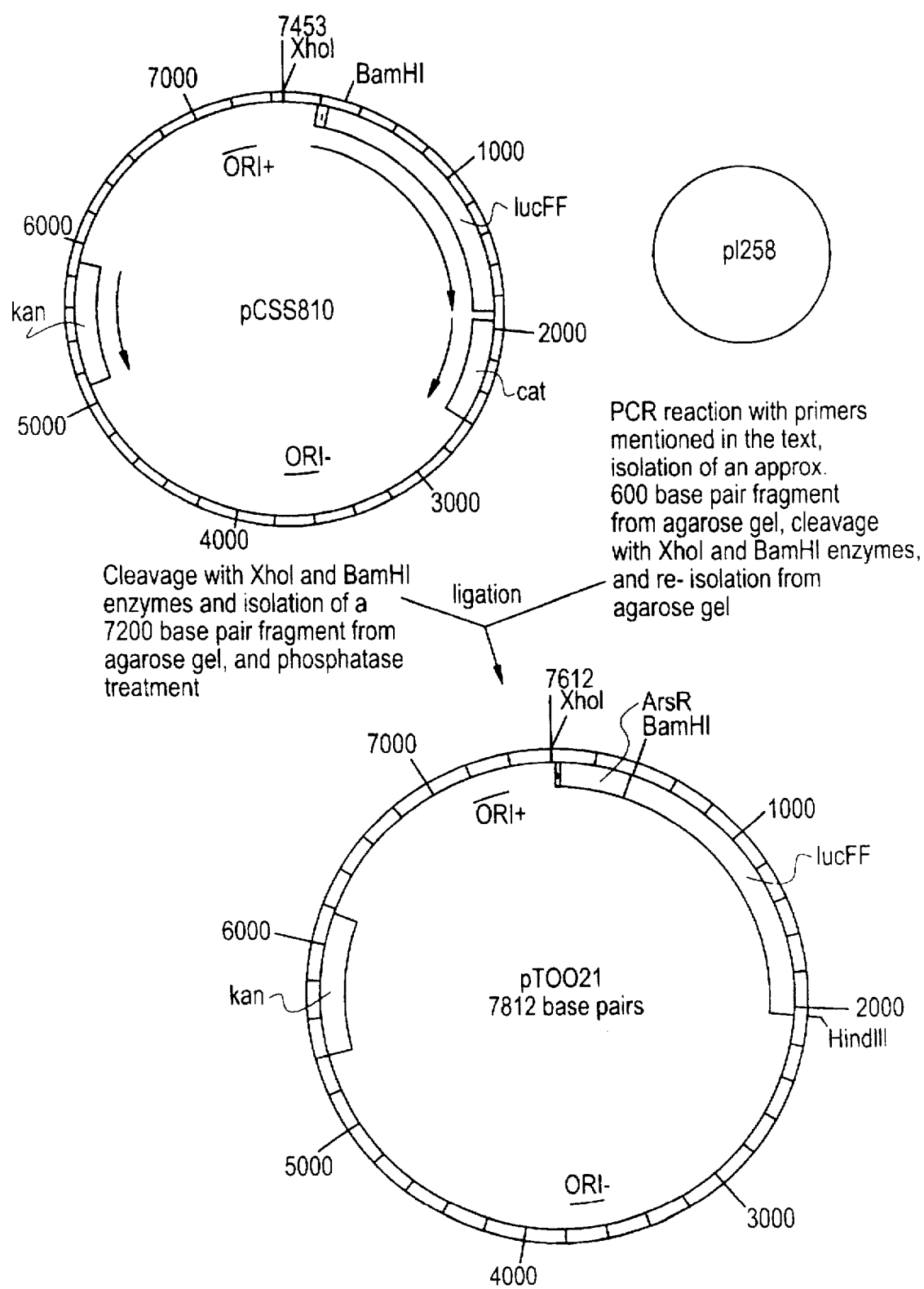
FIG. 11 depicts the structure and construction of the plasmid pTOO21.

Construction of the plasmid pTOO21 (FIG. 11)

The plasmid pTOO21 described in the invention was constructed using previously described recombinant DNA plasmids and generally known molecular biology techniques. The plasmid pCSS810 was cleaved with restriction enzymes XhoI and BamHI overnight at 37° C. To remove the terminal phosphate groups, the cut plasmid was treated by adding 0.1 unit of bovine intestinal alkaline phosphatase, and was kept at 37° C. for 30 min. The plasmid was separated from the uncut products by driving 0.8% low gelling temperature (LGT) agarose gel. Thereafter, a 7300 base pair fragment was separated from the gel by cutting it in ultraviolet light. The obtained gel fragment was melted at 65° C., and the cut plasmid was separated from it and was ligated by means of ligase enzyme to a PCR product cleaved with the same restriction enzymes. The said polymerase chain reaction product was obtained when arsR gene and the control region of ars operon were separated by a PCR reaction (polymerase chain reaction) from the plasmid pI258 isolated from a *Staphylococcus aureus* strain (NCTC 50581) (Ji, G. and Silver, S., 1992, J. Bacteriol., 174, 3684–3694). Primers of the following kinds were used in the reaction: 5'-ATCTCGAGTAAAATAACATAGACAATAATCT-3' SEQ ID No: 5 and 5'-TTAAGGATCCCCTCATCAACAGTCACCTGATT 3' SEQ ID No: 6, as well as Taq polymerase. After the reaction, a 380 base pair reaction product was separated from agarose gel, was cleaved with BamHI and XhoI enzymes, and was separated from the uncut products in the same manner as pCSS810 above. These DNA fragments were combined by means of ligase enzyme. It is to be noted here that the arsR gene and the control region of the ars operon were isolated in their entirety without including any parts unnecessary for control, a fact which is important in terms of the functioning of the present invention and produces a very sensitive arsenic detection.

The obtained construction was transferred in the manner described above into an *E. coli* MC1061 strain. The isolation of recombinant DNA plasmids was done on a small scale, as described (Maniatis et al., 1982), and the correct plasmid construction was ascertained by restriction enzyme cleavages. The isolation of the plasmid on a larger scale was done according to the instructions of the same manual. The plasmid pTOO21 thus constructed contains the initiation sites of DNA replication derived from both a gram positive bacterium and a gram negative bacterium. It is thus a so-called shuttle plasmid, which can also be transferred to other gram negative and gram positive bacteria. It was transferred to the *B. subtilis* BR151 strain by a method described earlier (Contente and Dubnau, 1979, Mol. Gen. Genet., 167, 251–258). By the use of a plasmid construction such as this it is possible to perform heavy metal determination in the organism in which the detection is the most sensitive possible, i.e. in which the metal transport mechanisms are active. The recombinant DNA plasmid pTOO21 was deposited on Jan. 12, 1995 with the depository DSM under deposit number 9666.

EXAMPLE 11

Figure 12:
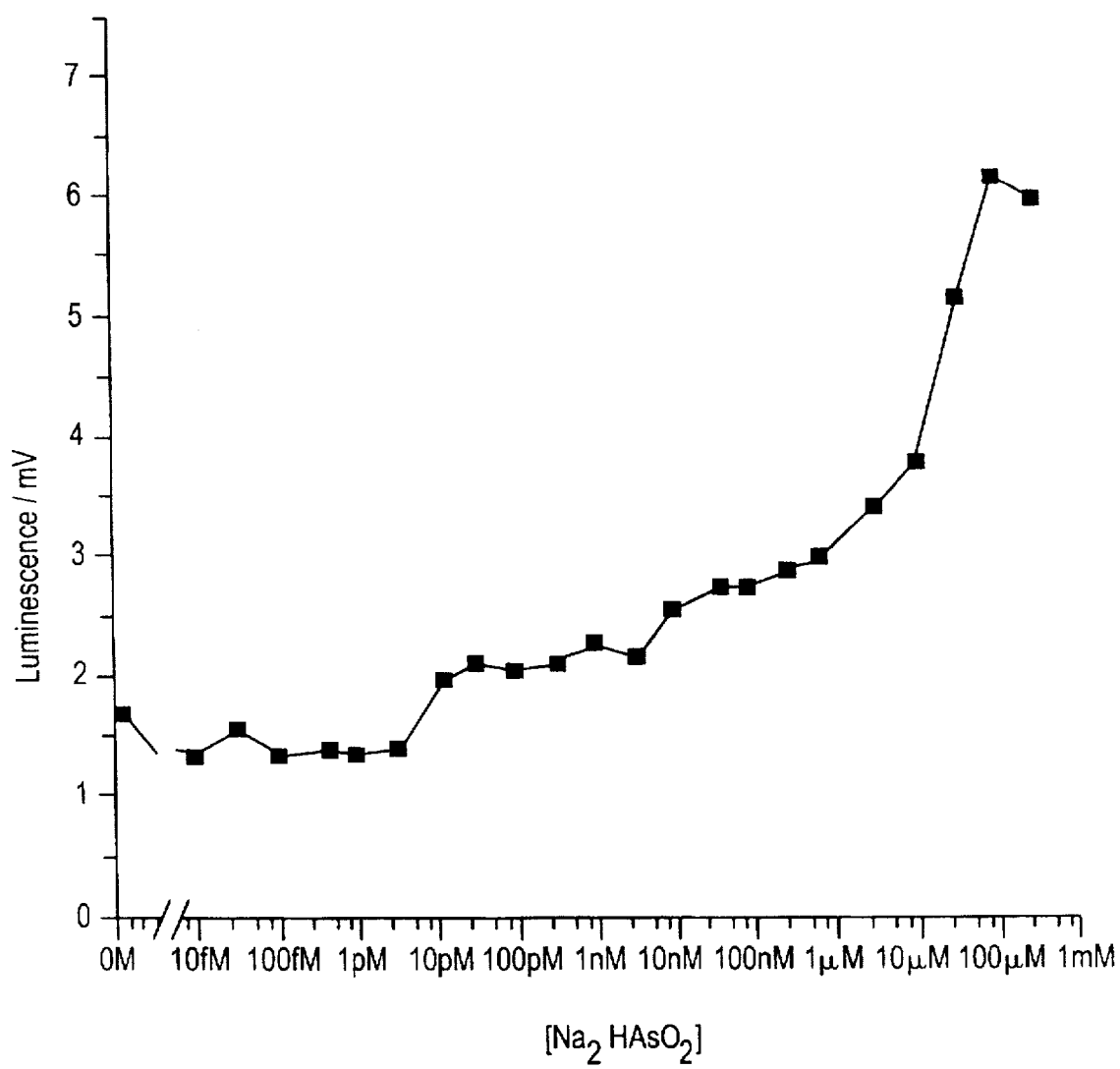
FIG. 12 depicts arsenite determination based on the strain *B. subtilis* BR151/pTOO21, measured on the basis of luminescence.

Arsenic determination based on the strain *B. subtilis* BR151/pTOO21, measured on the basis of luminescence Plasmid pTOO21 cloned *B. subtilis* BR151 cells grown overnight, in which OD600=1.5–2.0, were washed twice with M9 minimal culture solution (Maniatis et al., 1982) to which acid-hydrolyzed casein had been added 10 g/l. The cells were diluted 1:200 with the said culture solution. Various amounts of arsenic compounds were mixed with these cells. The samples, which were in luminometer tubes or on a 96-recess plate, were allowed to stand for 60 min at +30° C., whereafter 100 µl of 1 mM D luciferin was added to the samples and the luminescence of the samples was measured immediately. FIG. 12 depicts the luminescence of the bacteria as a function of the concentration of sodium arsenite.

EXAMPLE 12

Figure 13:
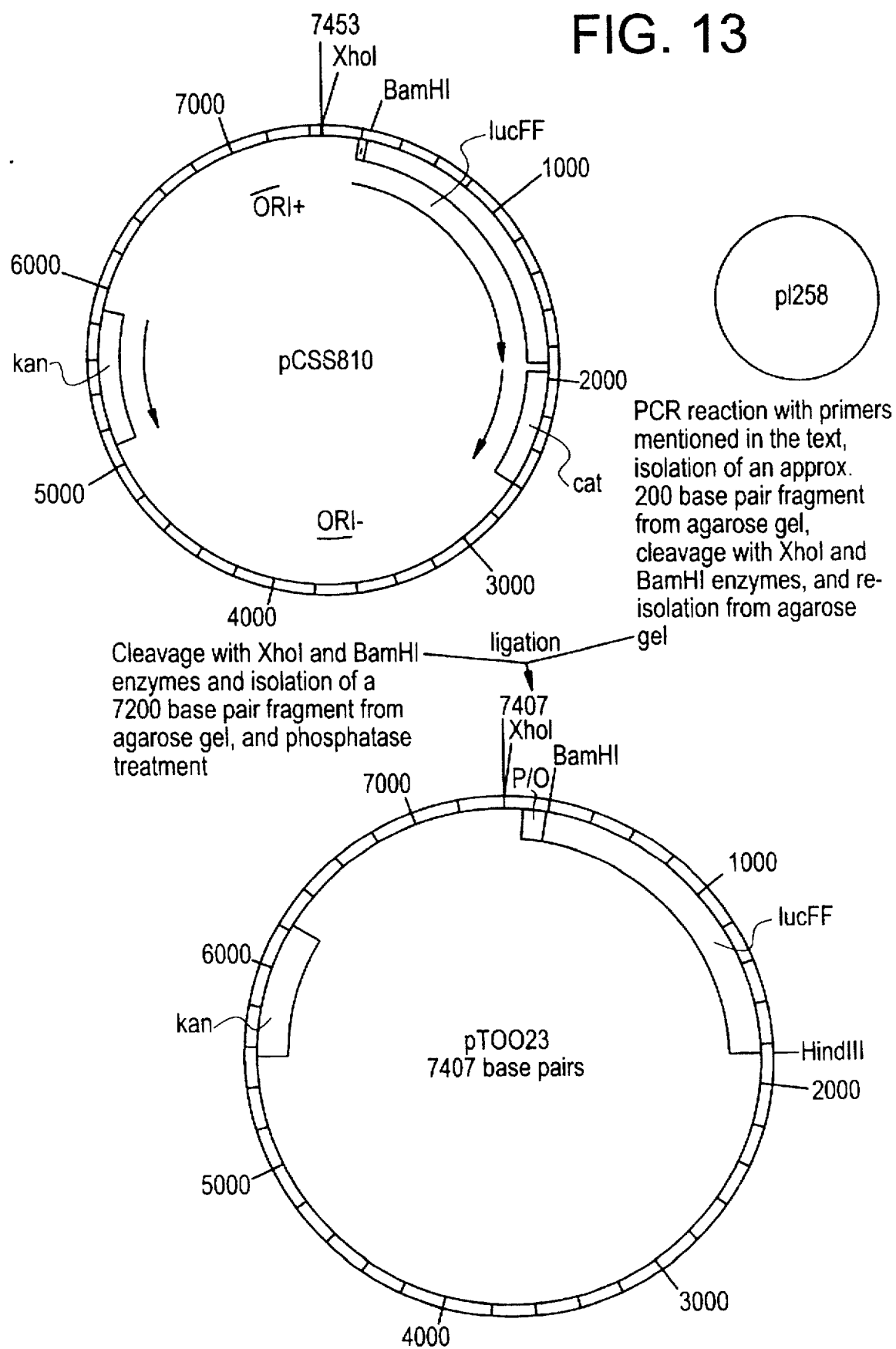
FIG. 13 depicts the structure and construction of the plasmid pTOO23.

Construction of the plasmid pTOO23 (FIG. 13)

The plasmid pTOO23 described in the invention was constructed by using previously described recombinant DNA plasmids and generally known molecular biology techniques. The plasmid pCSS810 was cleaved with restriction enzymes XhoI and BamHI overnight at 37° C. To remove the terminal phosphate groups the cut plasmid was treated by adding 0.1 unit of bovine intestinal alkaline phosphatase, and was kept at 37° C. for 30 min. The plasmid was separated from the uncut products by driving 0.8% low gelling temperature (LGT) agarose gel. Thereafter a fragment of 7300 base pairs was separated from the gel by cutting it in ultraviolet light. The obtained gel fragment was melted at 65° C., the cut plasmid was separated from it, and the plasmid was ligated by means of ligase enzyme to a PCR product cleaved with the same restriction enzymes. The said polymerase chain reaction product was obtained when the control region of the cad operon was separated by means of a PCR reaction (polymerase chain reaction) from the plasmid pI258 isolated from a *Staphylococcus aureus* strain (NCTC 50581) (Nucifora, G. et al., 1989, Proc. Natl. Acad. Sci. USA, 86, 3533–3548. Primers of the following kinds were used in the reaction: 5'-ATATCTCTTAACATAATAAAAGATTACAGTA-3'SEQ ID No:7 and 5'-TTAAGGACATATTATCATCCCATCTTCA-3' SEQ ID No: 8, as well as Taq polymerase. After the reaction, a 170 base pair reaction product was separated from agarose gel, was cleaved with BamHI and XhoI enzymes, and was separated from the uncut products in the same manner as pCSS810 above. These DNA fragments were combined by means of ligase enzyme.

The obtained construction was transferred in the manner described above to the *E. coli* MC1061 bacterial strain. The isolation of recombinant DNA plasmids was done on a small scale, as described in Maniatis et al., 1982, and the correct plasmid construction was ascertained by means of restriction enzyme cleavages. The isolation of the plasmid on a larger scale was done according to the instructions of the said publication. The plasmid pTOO23 thus constructed contains initiation sites of DNA replication derived both from a gram positive bacterium and a gram negative bacterium. It is thus a so-called shuttle plasmid, which can also be transferred to other gram negative bacteria or gram positive bacteria, such as *Staphylococcus aureus* (Schenk, S. and Laddaga, R. A., 1992, FEMS Microbiol. Lett., 94, 133–138). It can be transferred into the *B. subtilis* BR151 strain by a method described previously (Contente and Dubnau, 1979, Mol. Gen. Genet., 167, 251–258). By the use of a plasmid construction of this type, heavy metal determination can be done in the organism in which detection is the most sensitive possible, i.e. the metal transport mechanisms are active. The recombinant DNA plasmid pTOO23 was deposited on Jan. 12, 1995 with the depository DSM under deposit number 9667.

EXAMPLE 13

Figure 14:
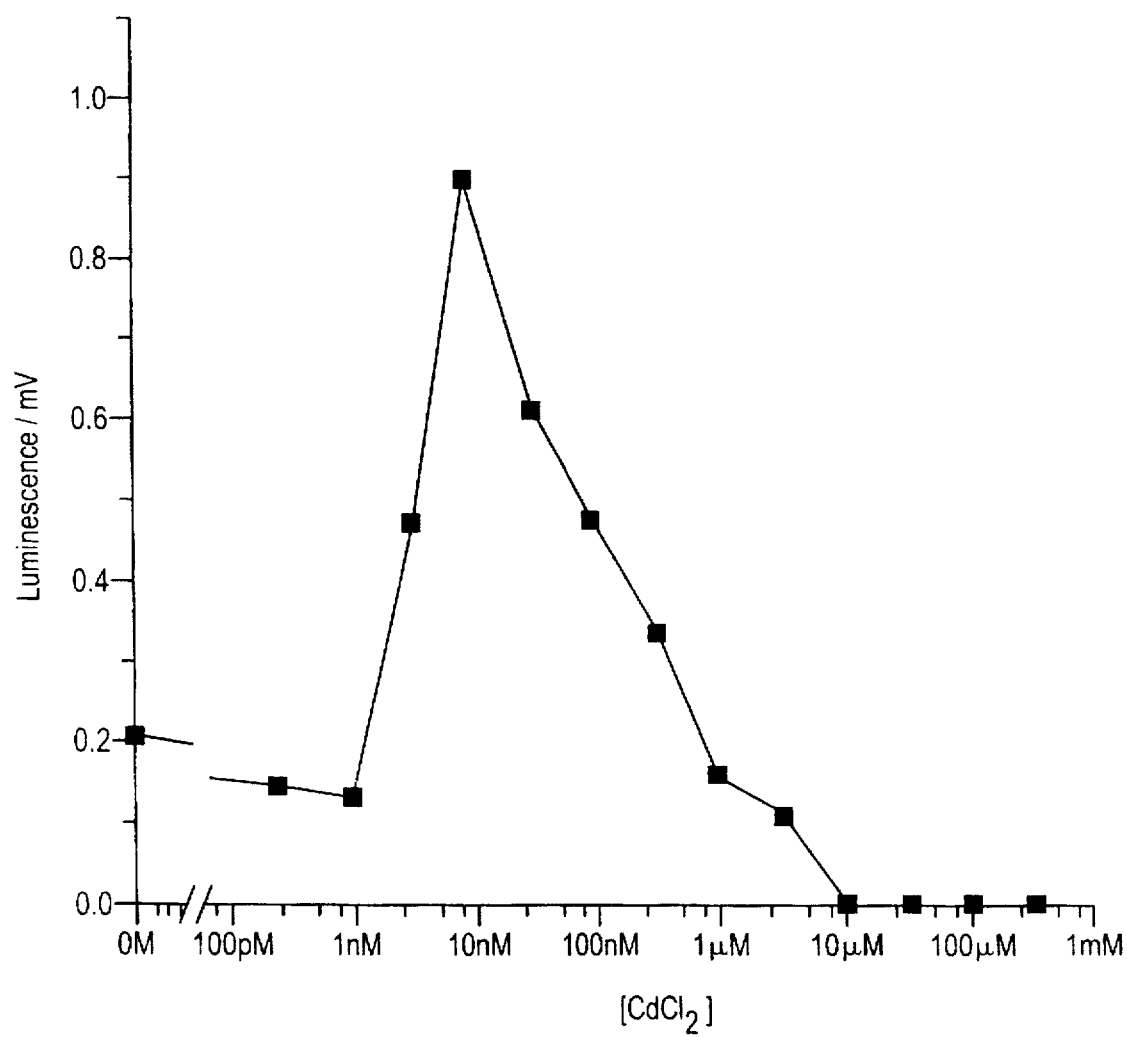
FIG. 14 depicts cadmium determination based on the strain *E. coli* MC1061/pTOO23, measured on the basis of luminescence.

Cadmium determination based on the strain *E. coli* MC1061/pTOO23, measured on the basis of luminescence Plasmid pTOO23 cloned *E. coli* MC1061 cells grown overnight, in which OD600=1.5–2.0, were washed twice with M9 minimal culture solution (Maniatis et al., 1982), to which acid-hydrolyzed casein had been added 10 g/l. The cells were diluted 1:200 with the said culture solution. Various amounts of cadmium compounds were mixed with these cells. The samples, which were in luminometer tubes or on a 96-recess plate, were allowed to stand for 60 minutes at +30° C., whereafter 100 µl of 1 mM D-luciferin was added to the samples, and the luminescence of the samples was measured immediately. FIG. 14 shows the bioluminescence of the bacteria as a function of the concentration of cadmium chloride.

EXAMPLE 14

Figure 15:
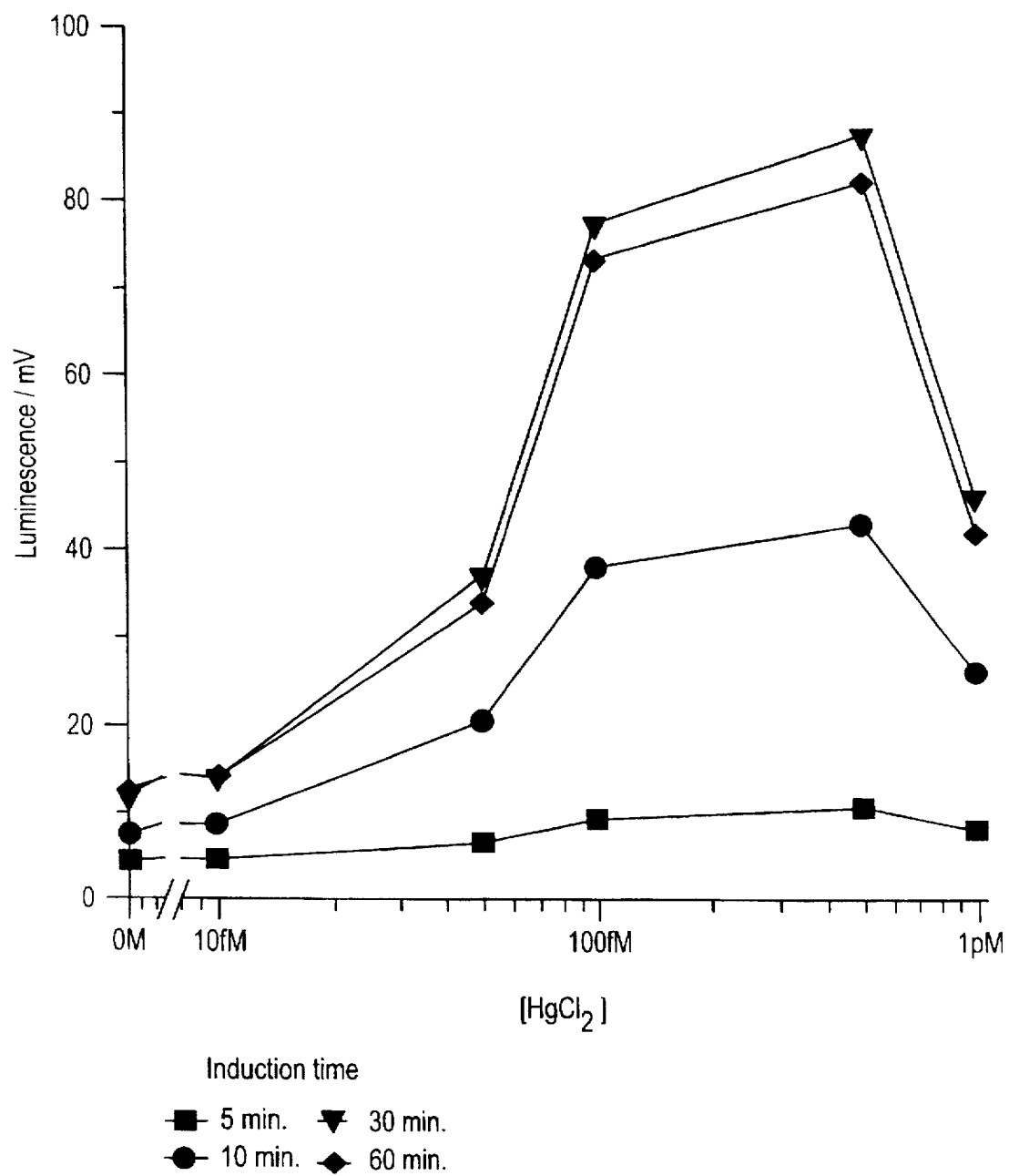
FIG. 15 depicts the effect of the induction time, i.e. contact time, on the production of light by the strain *E. coli* MC1061/pMV1.

Effect of the induction time, i.e. the contact time, on mercury determination when the *E. coli* MC1061/pMV1 strain is used.

pMV1 cloned *E. coli* MC1061 cells grown overnight, in which OD600=1.5–2.0, were washed twice with M9 minimal culture solution (Maniatis et al., 1982) to which acid-hydrolyzed casein had been added 10 g/l. The cells were diluted 1:200 with the said culture solution. Various amounts of mercury compounds were mixed with these cells. The samples, which were in luminometer tubes, were allowed to stand for 5, 10, 30 or 60 minutes at +30° C., whereafter 100 µl of 1 mM D-luciferin was added to the samples and the luminescence of the samples was measured immediately. FIG. 15 shows the bioluminescence of the bacteria as a function of the concentration of mercury chloride when different contact times were used.

---

We claim:

1. A method for determining a heavy metal in a sample comprising;
   a) providing a cell comprising a recombinant DNA plasmid, said plasmid comprising a gene coding for an insect luciferase or a green fluorescent protein (GFP) marker protein, wherein the copy number of said plasmid is under the control of a promoter regulatable by a heavy metal, and wherein said promoter controls the origin of replication of said plasmid;
   b) contacting said cell with a sample which contains said heavy metal;
   c) allowing said heavy metal to affect said cell, whereafter the amount of said marker protein is determined;
   d) comparing the amount of said marker protein with a control in which no metal was present or in which the heavy metal was present in a known amount, whereby the presence and/or amount of said heavy metal is determined.

2. The method according to claim 1, wherein said recombinant DNA plasmid further contains a DNA sequence which codes for a procaryotic cell protein or a eucaryotic cell protein, or a portion thereof.

3. The method according to claim 2, wherein the DNA sequence coding for said procaryotic cell protein or said eucaryotic cell protein is under the control of a regulatable promoter which is activated simultaneously with, or at a desired moment after, the activation of the promoter which controls the origin of the replication of the plasmid.

4. The method according to claim 1, wherein the promoter which controls the origin of the replication of the plasmid responds to mercury or an organic compound thereof.

5. The method according to claim 4, wherein the cell is *Escherichia coli* and the synthesis of said marker protein is regulated by the same type of heavy metal promoter as is the origin of replication or a promoter responding to a different heavy metal.

6. The method according to claim 1, wherein said recombinant DNA plasmid is pMV3 (DSM Deposit No. 8893).

7. A method for the determination of a heavy metal in a sample, comprising:
   a) providing a cell comprising a recombinant DNA plasmid, said plasmid comprising a gene coding for an insect luciferase or a green fluorescent protein (GFP) marker protein, and having a copy number between 1 and 2000/cell, wherein the expression of said marker protein sequence being a heavy metal, and wherein said promoter controls the origin of the replication of said plasmid;
   b) contacting said cell with a sample which contains said heavy metal;
   c) allowing said heavy metal to affect said cell, whereafter the amount of said marker protein is determined;
   d) comparing the amount of said marker protein with a control in which no metal was present or in which it was present in a known amount, whereby the presence and amount of said heavy metal is determined.

8. The method according to claim 7, wherein said recombinant DNA plasmid is pMV1 (DSM) Deposit No. 8708).

9. The method according to claim 7, wherein said recombinant DNA plasmid is pTOO21 (DSM Deposit No. 9666).

10. The method according to claim 7, wherein said recombinant DNA plasmid is pTOO23 (DSM Deposit No. 9667).

11. The method according to claim 7, wherein said cell is a gram-negative or gram-positive bacterium belonging to the group *Enterobacteriaccae* or the group *Bacillus*.

12. The method according to claim 11, wherein said cell is *Escherichia coli*.

13. The method according to claim 11, wherein said cell is *Bacillus subtilis*.

14. The method according to claim 7, wherein said cell has a metal transport mechanism from another organism transferred into said cell by genetic engineering.

15. The method according to claim 7, wherein the sample to be analyzed is in a liquid, or solid form, and the sample is of a biological or non-biological origin.

16. The method according to claim 7, wherein the cells containing the recombinant DNA plasmid have been freeze-dried, and before the determination they are rehydrated with a solution selected from the group consisting of a suitable buffer, the sample to be assayed, and a culture solution.

17. The method according to claim 7, wherein the plasmid further contains a DNA sequence which codes for a protein selected from the group consisting of phosphatases, galactosidases, oxyreductases, peroxydases and luciferases.

18. The method according to claim 17, wherein the protein is selected from the group consisting of insect luciferase, beta-galactosidase, alkaline phosphatase, horse radish peroxidase, beta-glucoronidase, and chloramphenicolacetyl transferase.

19. The method according to claim 7, wherein luciferin is added to the reaction in order to measure the amount of expressed insect luciferase in a bacterium.

20. The method according to claim 7, wherein the amount of said marker protein is further compared by utilizing another plasmid which is present in the same cell and has a gene coding, under the control of another control element, for a luciferase or a green fluorescent protein (GFP) producing a different wavelength maximum.

21. The method according to claim 7, wherein the sample is selected from the group consisting of milk, foodstuffs or their packaging materials, serum, urine, saliva, sediments, industrial process waters, waste waters, and environmental waters.

22. The plasmid pMV1 (DSM Deposit No. 8708).

23. The plasmid pMV3 (DSM Deposit No. 8893).

24. The plasmid pTOO21 (DSM Deposit No. 9666).

25. The plasmid pTOO23 (DSM Deposit No. 9667).

26. The method according to claim 1, wherein said cell is a gram-negative or gram-positive bacterium selected from the group consisting of *Enterobacteriaceae* and *Bacillus*.

27. The method according to claim 1, wherein the sample to be analyzed is in a liquid, or solid form, and the sample is of a biological or non-biological origin.

28. The method according to claim 1, wherein the cells containing the recombinant DNA plasmid have been freeze-dried, and before the determination they are rehydrated with a solution selected from the group consisting of a suitable buffer, the sample to be assayed and a culture solution.

29. The method according to claim 1, wherein the plasmid further contains a DNA sequence which codes for a protein selected from the group consisting of phosphatases, galactosidases, oxyreductases, peroxydases and luciferases.

30. The method according to claim 1, wherein the amount of said marker protein is further compared by utilizing another plasmid which is present in the same cell and has a gene under the control of another control unit coding for a luciferase or a green fluorescent protein (GFP) producing a different wavelength maximum.

31. The method according to claim 1, wherein the sample is selected from the group consisting of milk, foodstuffs or their packaging materials, serum, urine, saliva, sediments, industrial process waters, waste waters, and environmental waters.

32. The method according to claim 3, wherein luciferin is added to the reaction in order to measure the amount of expressed insect luciferase in a bacterium.

33. A method of claim 7, wherein said cells comprising the recombinant DNA plasmid are immobilized, freeze-dried or kept in solution.

34. The method according to claim 1, wherein the DNA sequence coding for said marker protein is under the control of a regulatable promoter which is activated simultaneously with, or at a desired moment after, the activation of the promoter which controls the origin of the replication of said plasmid.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CTTAAGGATC  CCCTCATAGT  TAATTTCTCC  TCTTTTGAAT  TTGGATTGGA  TA                52
```

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CATATCTCGA GCTAAGGCAT AGCTGACCT                                        29

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ATATGGATCC AGCAAAGGAG AAGAAC                                          26

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AATTAAGCTT GGAAGTCTGG ACAT                                              24

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

ATCTCGAGTA AAATAACATA GACAATAATC T                                  31

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TTAAGGATCC CCTCATCAAC AGTCACCTGA TT                                32

( 2 ) INFORMATION FOR SEQ ID NO:7:

( i ) SEQUENCE CHARACTERISTICS:

(A) LENGTH: 31 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

ATATCTCTTA ACATAATAAA AGATTACAGT A                                31

(2) INFORMATION FOR SEQ ID NO:8:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:8:

TTAAGGACAT ATTATCATCC CATCTTCA                                    28